(12) United States Patent
Shaler et al.

(10) Patent No.: US 11,740,234 B2
(45) Date of Patent: Aug. 29, 2023

(54) BIOMARKERS FOR DETECTION OF BURKHOLDERIA PSEUDOMALLEI

(71) Applicant: SRI International, Menlo Park, CA (US)

(72) Inventors: Thomas A. Shaler, Fremont, CA (US); Hua Lin, Fremont, CA (US)

(73) Assignee: SRI International, Menlo Park, CA (US)

( * ) Notice: Subject to any disclaimer, the term of this patent is extended or adjusted under 35 U.S.C. 154(b) by 606 days.

(21) Appl. No.: 16/821,285

(22) Filed: Mar. 17, 2020

(65) Prior Publication Data

US 2020/0362385 A1    Nov. 19, 2020

Related U.S. Application Data

(60) Provisional application No. 62/849,607, filed on May 17, 2019.

(51) Int. Cl.
| | |
|---|---|
| *C12Q 1/04* | (2006.01) |
| *C12M 1/12* | (2006.01) |
| *G01N 33/543* | (2006.01) |
| *A61K 45/06* | (2006.01) |

(52) U.S. Cl.
CPC ....... *G01N 33/54388* (2021.08); *C12M 25/14* (2013.01); *C12Q 1/04* (2013.01); *A61K 45/06* (2013.01); *C12Q 2563/119* (2013.01)

(58) Field of Classification Search
None
See application file for complete search history.

(56) References Cited

U.S. PATENT DOCUMENTS

2015/0167056 A1*   6/2015   Schupp ............... C12Q 1/689
                                                    435/6.12
2016/0146812 A1*   5/2016   AuCoin ................. C12Q 1/04
                                                    435/7.1

OTHER PUBLICATIONS

Burkholderia pseudomallei Genome Database (Windsor, GL; et al; Bioinformatics, 24, 2803-2804, 2008)https://www.burkholderia.com/) (Year: 2008).*
Felgner P.L. et al. "A Burkholderia pseudomallei protein microarray reveals serodiagnostic and cross-reactive antigens." Proc Natl Acad Sci USA. 2009; 106(32):13499-504.
Kohler, D. et al. "Rapid and Sensitive Multiplex Detection of Burkholderia pseudomallei-Specific Antibodies in Melioidosis Patients Based on a Protein Microarray Approach." PLOS Neglected Tropical Diseases. 2016; vol. 10(7).

(Continued)

*Primary Examiner* — David W Berke-Schlessel
(74) *Attorney, Agent, or Firm* — Dicke, Billig & Czaja, PLLC

(57) ABSTRACT

Various examples are directed to kits, apparatuses, and methods for determining a presence of *Burkholderia pseudomallei* (BP) in a biological sample. An example method includes causing a physical interaction between a biological sample from a subject and a set of first agents by exposing the biological sample to the set of first agents, the set of first agents being specific to one or more of a set of BP biomarkers associated with one or more proteins released from BP or associated with other molecules released from BP. The method further includes determining a presence of BP in the biological sample based on detected binding between one or more of the set of first agents and the one or more of the set of BP biomarkers.

20 Claims, 16 Drawing Sheets

Specification includes a Sequence Listing.

(56) References Cited

OTHER PUBLICATIONS

Limmathurotsakul, D., Golding, N., Dance, D. et al. "Predicted global distribution of Burkholderia pseudomallei and burden of melioidosis." Nat Microbiol 1, 15008 (2016). Abstract Only.
Limmathurotsakul, D. et al. "Role and Significance of Quantitative Urine Cultures in Diagnosis of Melioidosis." J. of Clinical Microbiology. 2005; 43(5): 2274-2275).

* cited by examiner

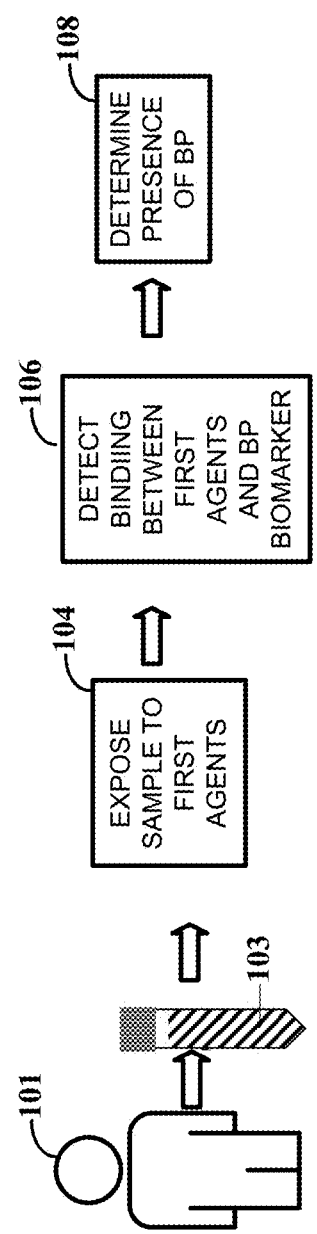

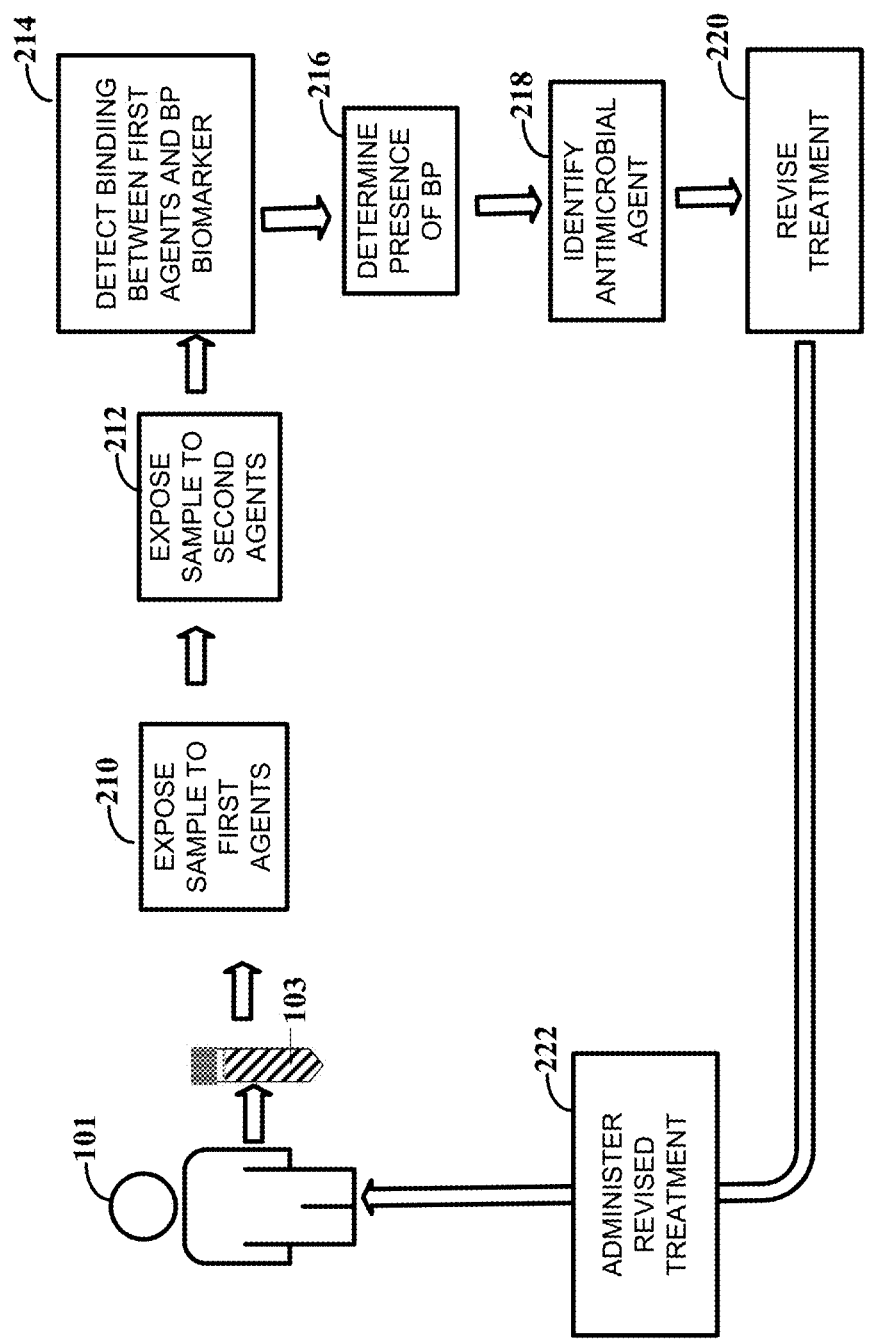

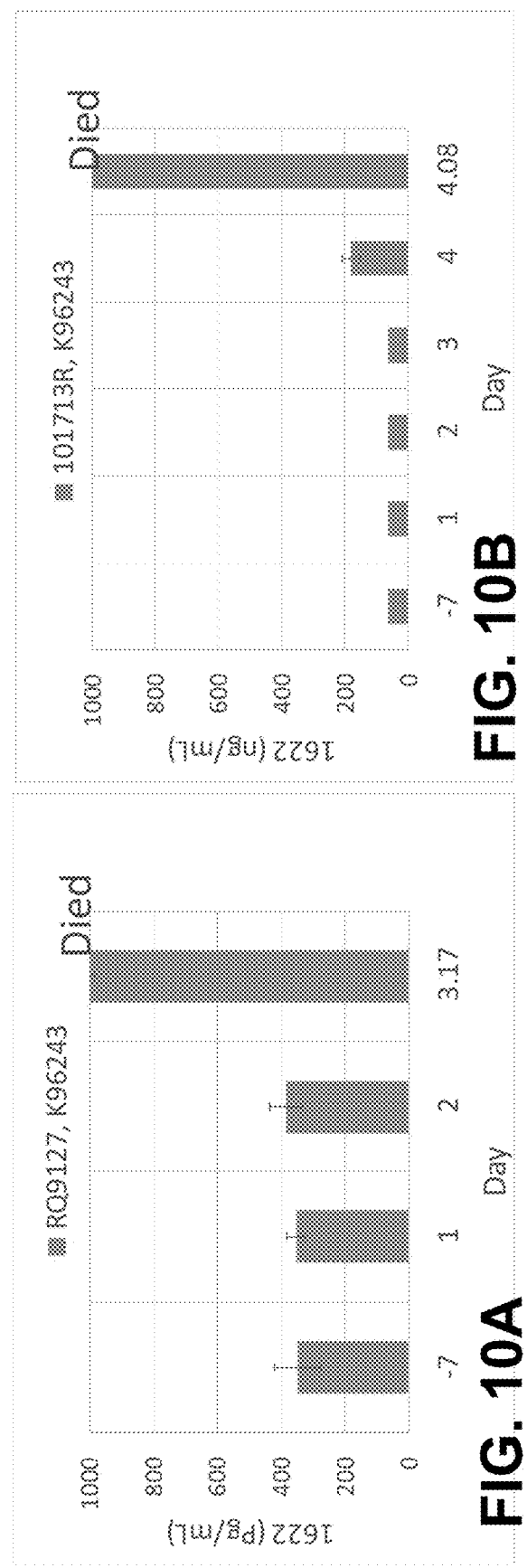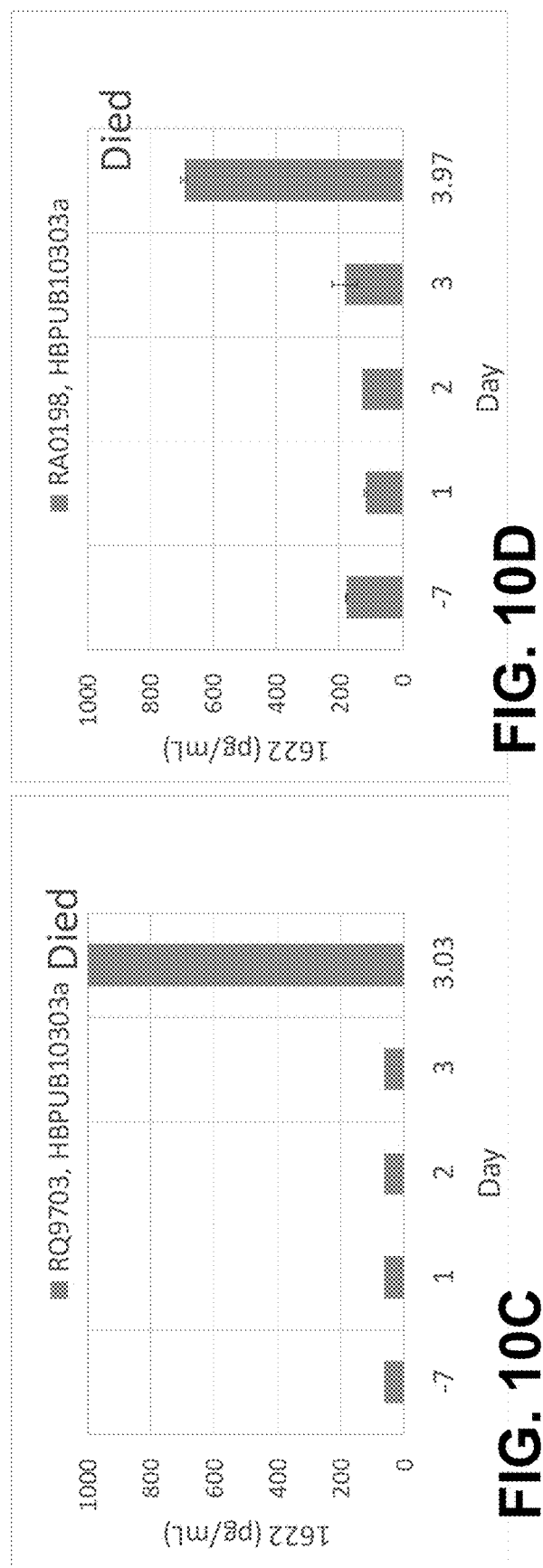

SEQUENCE LISTING

```
<160> NUMBER OF SEQ ID NOS: 17

<210> SEQ ID NO 1
<211> LENGTH: 365
<212> TYPE: PRT
<213> ORGANISM: Burkholderia pseudomallei

<400> SEQUENCE: 1

Met Lys Ser Leu Phe Asp Ala Pro Ser Ser Arg Pro Arg Ala Arg Ala
1               5                   10                  15

Ala Leu Thr Leu Gly Ala Ala Ala Thr Leu Thr Ala Ser Phe Ala Ala
            20                  25                  30

Leu Leu Ala Pro Met Asn Ala Asp Ala His Gly Ala Val Gly Phe Pro
        35                  40                  45

Ile Ala Arg Gln Tyr Gln Cys Arg Leu Glu Gly Gly Tyr Trp Asp Pro
    50                  55                  60

Pro Asn Gly Ser Ala Ile Pro His Asp Asp Cys Arg Ala Ala Tyr Arg
65                  70                  75                  80

Ala Gly Asn Asn Ser Ala Tyr Pro Phe Thr Gln Trp Asn Glu Val Ser
                85                  90                  95

Ala Asn Pro Val Gly Gln Gly Asn Asp Leu Ala Gln Leu Lys Ala Ala
            100                 105                 110

Val Pro Asp Gly Leu Leu Cys Ala Gly Gly Asp Thr Ser Lys Ala Gly
        115                 120                 125

Leu Asp Lys Ala Pro Ala Ser Val Trp Arg Lys Thr Gln Leu Thr Pro
    130                 135                 140

Asn Asn Gly His Ile Glu Leu Gln Trp Glu Asn Thr Thr Ala His Asn
145                 150                 155                 160

Pro Ala Arg Met Arg Val Phe Ile Ser Lys Pro Ser Tyr Asp Pro Ser
                165                 170                 175

Arg Pro Leu Arg Trp Asp Asp Leu Gln Gln Ile Tyr Asp Ala Pro Ala
            180                 185                 190

Pro Ala Pro Val Pro Ala Asn Gly Ala Gly His Leu Pro Gly Ser Ile
        195                 200                 205

Gln Ser Phe Tyr Lys Leu Asp Val Thr Leu Pro Ala Gly Arg Thr Gly
    210                 215                 220

Asp Ala Val Leu Tyr Ser Tyr Trp Gln Arg Ile Asp Ala Gly Asn Glu
225                 230                 235                 240

Gly Phe Phe Asn Cys Ser Asp Val Thr Ile Ala Ala Asp Glu Arg Ala
                245                 250                 255

Ser Gly Phe Pro Trp Val Ala Ala Arg Ala Phe Val Glu Pro Gly Ile
            260                 265                 270
```

Ala Pro Arg Ala Gly Gln Gln Val Arg Phe Arg Val Met Ile Asn Asp
          275                 280                 285

Ala Arg Gly Ala Glu Val Val Asp Val Arg Gln Pro Ile Thr Pro Tyr
290                 295                 300

Asn Ala Glu Arg Ser Val Trp Ala Lys Gln Ile Ala Asp Gln Val Asn
305                 310                 315                 320

Gly Arg Tyr Gly Asn Ile Ala Lys Ile Gly Val Arg Ser Gly Asn Thr
              325                 330                 335

Ile Tyr Phe Asp Ala Thr Asn Leu Asp Ala Asn Lys Val Trp Leu Gln
              340                 345                 350

Pro Asn Tyr Ser Ser Ala Leu Ser Val Val Gly Ala Lys
          355                 360                 365

<210> SEQ ID NO 2
<211> LENGTH: 256
<212> TYPE: PRT
<213> ORGANISM: Burkholderia pseudomallei

<400> SEQUENCE: 2

Met Lys Ser Ser Lys Ile Ser Lys Thr Leu Ile Cys Ser Leu Leu Ala
1               5                   10                  15

Phe Ser Ala Thr Ala Phe Ser Ile His Pro Val Leu Ala Ala Ser Pro
              20                  25                  30

Gln Gly Gly Lys Ile Ala Thr Thr Ile Gln Ala Ala Gly Gln Thr
          35                  40                  45

Asp Ile Ala Ala Leu Phe Lys Lys Thr Asn Phe Gln Met Asp Ser Ala
      50                  55                  60

Ala Glu Tyr Gly Lys Val Met Gln Ala Ile Ala Ala Asn Glu Ser Ala
65                  70                  75                  80

Ala Val Thr Tyr Val Gln Asp Ser Arg Leu Ser Ala Thr Glu Val Gln
              85                  90                  95

Thr Thr His Pro Ile Trp Ser Gly Val Gln Asn Gly Asp Arg Leu Gly
          100                 105                 110

Val Ser Trp Ser Gly Gly Asp Phe Gln His Gln Arg Ile Phe Val Tyr
      115                 120                 125

Glu Gly Asn Gly Asn Ala Gly Lys Trp Lys Lys Ala Glu Ala Ala Asp
130                 135                 140

Ile Pro Leu Lys Gln Gly Gly Ala Pro Ser Ile Leu Asn Gln Thr Pro
145                 150                 155                 160

Leu Met Pro Leu Met Pro Gln Gln Gln Val Arg Glu Thr Ser Ala Ser
              165                 170                 175

Ala Lys Ser Val Ala Asp Val Val Ser Val Ser Leu Tyr Arg Arg Val
          180                 185                 190

Thr Gly Asn Ile Asp Ile Tyr Thr Val Lys Val Gly Ser Arg Ile Gln
      195                 200                 205

Gly Ile Tyr Gly Val Gly Met Thr Ala Pro Gly Trp Ile Gln Ala Asp
210                 215                 220

Gly Val Gly Thr Asp Ile Val Val Phe Gln Val Arg Ala Ser Gly Thr
225                 230                 235                 240

Pro Gly Leu Phe Tyr Ser Gly Val Ala Ser Ala Thr Val Ile Arg Glu
              245                 250                 255

<210> SEQ ID NO 3
<211> LENGTH: 171
<212> TYPE: PRT
<213> ORGANISM: Burkholderia pseudomallei

<400> SEQUENCE: 3

```
Met Arg Asn Arg Lys Phe Val Pro Phe Val Ala Leu Ala Phe Ala
1               5                   10                  15

Ala Ala Ala Ala Thr Pro Ala Leu Ala Val Thr Val Val Arg Val Asp
            20                  25                  30

Gly Gln Pro Met Asn Pro Asn Gly Glu Pro Phe Ser Ala Thr Ser Ala
            35                  40                  45

Pro Leu Glu Thr Thr Leu Ser Lys Gly Ser Ile Ser Ala Asn Cys Val
    50                  55                  60

Ala Thr Phe Asn Gly Thr Ile Thr Pro Ala Gly Ile Val Asn Ile Thr
65                  70                  75                  80

Ser Thr Thr Phe Thr Gly Thr Asn Ser Leu Cys Gly Leu Ile Lys Gly
                85                  90                  95

Ser Ala Ser Gly Thr Asn Pro Trp Thr Gly Gln Ala Asp Ser Ala Thr
            100                 105                 110

Gln Leu Thr Ile Asn Asn Ala Gln Val Asn Val Thr Leu Leu Gly Gln
        115                 120                 125

Cys Gly Pro Ser Lys Val Val Thr Ser Trp Thr Asp Ala Asn Ser Ser
130                 135                 140

Leu Thr Phe Ser Asn Ala Ala Leu Ala Pro Asp Cys Lys Val Thr Gly
145                 150                 155                 160

Thr Val Val Thr Ser Pro Lys Phe His Val Gln
                165                 170
```

<210> SEQ ID NO 4
<211> LENGTH: 457
<212> TYPE: PRT
<213> ORGANISM: Burkholderia pseudomallei

<400> SEQUENCE: 4

```
Met Glu Arg Thr Met Asn Phe Ser Met Leu Ser Arg Ile Val Pro Arg
1               5                   10                  15

Ala Leu Ala Ala Gly Cys Leu Phe Ala Ala Ala Gly Ala Ser Gln Ala
            20                  25                  30

Ala Gly Val Tyr Ala Pro Tyr Val Asp Val Thr Leu Tyr Pro Thr Pro
        35                  40                  45

Leu Val Asp Gln Ile Gly Val Gln Gln Gly Ile Gln Gln Phe Met Leu
    50                  55                  60

Ala Phe Val Val Ser Gly Gly Asn Gln Cys Thr Pro Ser Trp Gly Gly
65                  70                  75                  80

Val Gln Pro Ile Gly Asn Gly Ala Thr Gly Asp Leu Leu Asp Lys Ile
                85                  90                  95

Ala Thr Ser Val Thr Ala Tyr Arg Ala Lys Gly Gly Asp Val Ala Val
            100                 105                 110

Ser Phe Gly Gly Ala Ala Gly Gln Pro Leu Met Gln Ala Cys Ser Ser
        115                 120                 125

Val Ala Ala Leu Lys Gly Ala Tyr Gln Thr Val Ile Asp Thr Tyr Ser
130                 135                 140

Leu Thr His Val Asp Phe Asp Ile Glu Gly Ala Ser Gln Gln Asp Ser
145                 150                 155                 160

Ala Ala Val Ala Arg Asn Phe Gln Ala Val Gln Leu Gln Ala Asp
            165                 170                 175

Tyr Ala Ala Lys Gly Lys Pro Leu His Val Thr Leu Thr Leu Pro Ala
            180                 185                 190
```

-continued

Met Pro Thr Gly Leu Val Gln Asp Gly Leu Asn Val Leu Asn Ala Ala
            195                 200                 205

Leu Ala Asn Asn Val Thr Leu Asp Ala Val Asn Ile Met Thr Met Asp
    210                 215                 220

Tyr Gly Pro Ser Gly Ile Asp Met Gly Ala Ala Ile Ser Ala Ala
225                 230                 235                 240

Gln Gly Leu Tyr Ser Gln Leu Asp Thr Ala Tyr Lys Ser Ala Gly Lys
                245                 250                 255

Pro Gln Thr Asp Ala Gln Leu Lys Gln Leu Val Gly Val Thr Pro Met
            260                 265                 270

Ile Gly Val Asn Asp Val Ala Gly Glu Ile Phe Thr Leu Ala Asn Ala
            275                 280                 285

Gln Ser Val Gln Thr Met Ala Ala Asn Asn Tyr Gly Phe Val Gly
            290                 295                 300

Ile Trp Ser Ile Thr Arg Asp Lys Ala Cys Asp Gly Ser Ser Gln Tyr
305                 310                 315                 320

Ala Ser Pro Ile Cys Ser Gly Val Ala Gln Gln Pro Tyr Ala Phe Ser
                325                 330                 335

Ser Val Phe Lys Gln Leu Gly Gly His Trp Gly Ala Gly Val Thr Gln
            340                 345                 350

Asp Pro Asn Tyr Gly Gly Gly Ser Asp Gly Gly Gly Lys Pro Gln Pro
            355                 360                 365

Gly Ala Pro Trp Ser Ala Thr Gln Val Tyr Thr Ala Gly Ala Thr Val
            370                 375                 380

Thr Tyr Gln Gly Thr Thr Tyr Gln Ala Gln Trp Thr Gln Gly Asp
385                 390                 395                 400

Ile Pro Gly Gln Ala Ser Val Trp Lys Pro Val Gly Gly Asn Val Pro
                405                 410                 415

Ala Trp Ser Ser Thr Thr Ala Tyr Pro Gly Gly Ala Cys Val Thr Tyr
            420                 425                 430

Gln Gly Ala Lys Tyr Cys Ala Lys Trp Trp Thr Gln Gly Asp Val Pro
            435                 440                 445

Ser Ala Gly Gly Pro Trp Ala Arg Ala
            450                 455

<210> SEQ ID NO 5
<211> LENGTH: 388
<212> TYPE: PRT
<213> ORGANISM: Burkholderia pseudomallei

<400> SEQUENCE: 5

Met Leu Gly Ile Asn Ser Asn Ile Asn Ser Leu Val Ala Gln Gln Asn
1               5                   10                  15

Leu Asn Gly Ser Gln Gly Ala Leu Ser Gln Ala Ile Thr Arg Leu Ser
            20                  25                  30

Ser Gly Lys Arg Ile Asn Ser Ala Ala Asp Ala Ala Gly Leu Ala
            35                  40                  45

Ile Ala Thr Arg Met Gln Thr Gln Ile Asn Gly Leu Asn Gln Gly Val
    50                  55                  60

Ser Asn Ala Asn Asp Gly Val Ser Ile Leu Gln Thr Ala Ser Ser Gly
65                  70                  75                  80

Leu Thr Ser Leu Thr Asn Ser Leu Gln Arg Ile Arg Gln Leu Ala Val
                85                  90                  95

Gln Ala Ser Asn Gly Pro Leu Ser Ala Ser Asp Ala Ser Ala Leu Gln

```
            100                 105                 110
Gln Glu Val Ala Gln Gln Ile Ser Glu Val Asn Arg Ile Ala Ser Gln
        115                 120                 125

Thr Asn Tyr Asn Gly Lys Asn Ile Leu Asp Gly Ser Ala Gly Thr Leu
    130                 135                 140

Ser Phe Gln Val Gly Ala Asn Val Gly Gln Thr Val Ser Val Asp Leu
145                 150                 155                 160

Thr Gln Ser Met Ser Ala Ala Lys Ile Gly Gly Met Val Gln Thr
                165                 170                 175

Gly Gln Thr Leu Gly Thr Ile Lys Val Ala Ile Asp Ser Ser Gly Ala
            180                 185                 190

Ala Trp Ser Ser Gly Ser Thr Gly Gln Glu Thr Thr Gln Ile Asn Val
        195                 200                 205

Val Ser Asp Gly Lys Gly Gly Phe Thr Phe Thr Asp Gln Asn Asn Gln
    210                 215                 220

Ala Leu Ser Ser Thr Ala Val Thr Ala Val Phe Gly Ser Ser Thr Ala
225                 230                 235                 240

Gly Thr Gly Thr Ala Ala Ser Pro Ser Phe Gln Thr Leu Ala Leu Ser
                245                 250                 255

Thr Ser Ala Thr Ser Ala Leu Ser Ala Thr Asp Gln Ala Asn Ala Thr
            260                 265                 270

Ala Met Val Ala Gln Ile Asn Ala Val Asn Lys Pro Gln Thr Val Ser
        275                 280                 285

Asn Leu Asp Ile Ser Thr Gln Thr Gly Ala Tyr Gln Ala Met Val Ser
    290                 295                 300

Ile Asp Asn Ala Leu Ala Thr Val Asn Asn Leu Gln Ala Thr Leu Gly
305                 310                 315                 320

Ala Ala Gln Asn Arg Phe Thr Ala Ile Ala Thr Thr Gln Ala Gly
                325                 330                 335

Ser Asn Asn Leu Ala Gln Ala Gln Ser Gln Ile Gln Ser Ala Asp Phe
            340                 345                 350

Ala Gln Glu Thr Ala Asn Leu Ser Arg Ala Gln Val Leu Gln Gln Ala
        355                 360                 365

Gly Ile Ser Val Leu Ala Gln Ala Asn Ser Leu Pro Gln Gln Val Leu
    370                 375                 380

Lys Leu Leu Gln
385

<210> SEQ ID NO 6
<211> LENGTH: 645
<212> TYPE: PRT
<213> ORGANISM: Burkholderia pseudomallei

<400> SEQUENCE: 6

Met Thr Glu Val Phe Arg Lys Thr Arg Arg Trp Ser Ala Val Ala Ala
1               5                   10                  15

Leu Ser Ala Phe Val Gly Leu Ala Gly Ala Ser Ala Asn Thr Gln
                20                  25                  30

Pro Met Gln Pro Thr Gln Lys Gln Ala Arg Met Pro Arg Leu Pro
            35                  40                  45

Gln Asn Leu Pro Val Ser Pro Glu Gln Ala Glu Tyr Asn Leu Pro Leu
        50                  55                  60

Ser Glu Gln Asp Arg Ala Ala Leu Thr Arg Pro Ser Pro Leu Lys Gln
65                  70                  75                  80
```

```
Pro Ala Lys Arg Gly Lys Arg Ser Ala Pro Gly Ala Asp Cys Arg Asp
                85                  90                  95
Met Ser Val Met Thr Gln Tyr Arg Gly Ala Ala Leu Ala Asp Tyr Ile
            100                 105                 110
Ala Asn Leu Pro Asp Tyr Glu Cys His Tyr Gly Leu Phe Ser Val Asp
        115                 120                 125
Lys Thr Leu Ala Ala Gln Ile Phe Ser Ala Glu Asn Val His Ala Val
    130                 135                 140
Ala Ser Arg Phe Val Gln Asp Ile Tyr Arg Tyr Asp Ala Ser Asn Leu
145                 150                 155                 160
Ile Leu Val Asn Leu Leu Ile Tyr Leu Arg Ser Ala Tyr Tyr Gln Tyr
                165                 170                 175
Asp Val Ser Gly Ile Ala Asn Pro Ile Pro Asn Leu Ala Val Trp Leu
            180                 185                 190
Arg Pro Tyr Ile Lys Gln Ser Leu Glu Gly Ala Ala Leu Tyr Arg Glu
        195                 200                 205
Asn Ala Arg Ala Pro Ser Thr Ala Asn Glu Leu Met Lys Leu Ile Thr
    210                 215                 220
Asn Met Lys Asp Glu Ala Phe Tyr Leu Pro Thr Leu Lys Ala Arg Ile
225                 230                 235                 240
Ala Phe Tyr Thr Ala Ser Ala Thr Asn Pro Gln Ala Ala Pro Leu
                245                 250                 255
Leu Gln Pro Ser Ala Ala Gly Gly Phe Thr Gly Leu Leu Thr Val Phe
            260                 265                 270
Phe Tyr Ala His Gln Arg Ser Gly Ala Gln Pro Met Leu Asp Ser Asp
        275                 280                 285
Ala Thr Leu Pro Glu Thr Leu Asn Arg Phe Val Thr Ala Asn Arg Ala
    290                 295                 300
Ser Leu Ser Asn Thr Ser Ala Ala Tyr Gln Leu Ala Asp Ala Ala Arg
305                 310                 315                 320
Glu Thr Phe Arg Phe Leu Arg Tyr Pro Ala Gln Lys Pro Arg Val Lys
                325                 330                 335
Lys Met Ile Gln Asp Met Leu Ala Ser Thr Ser Met Thr Gly Ala Asp
            340                 345                 350
Ser Asp Leu Trp Leu Ala Ala Ala Glu Ala Val Asp Tyr Gly Asp Ser
        355                 360                 365
Gly Asn Cys Ala Asp Tyr Gly Thr Cys Asp Tyr Lys Lys Arg Leu Thr
    370                 375                 380
Asp Ala Val Leu Thr His Arg Tyr Ala Cys Asn Ala Gly Val Arg Ile
385                 390                 395                 400
Leu Ala Gln Asp Met Thr Met Pro Gln Leu Gln Ser Val Cys Thr Ser
                405                 410                 415
Val Ala Gln Gln Asp Asp Tyr Phe His Arg Met Met Lys Thr Gly Arg
            420                 425                 430
Lys Pro Val Ala Gly Asp Arg Asn Asp Thr Ile Glu Leu Val Ile Phe
        435                 440                 445
Asp Asp Tyr Ala Asn Tyr Arg Lys Tyr Ala Ser Val Ile Tyr Gly Ile
    450                 455                 460
Ser Thr Asp Asn Gly Gly Met Tyr Leu Glu Gly Asp Pro Ser Ala Pro
465                 470                 475                 480
Gly Asn Gln Ala Arg Phe Ile Ala His Glu Ala Ser Trp Leu Arg Pro
                485                 490                 495
Glu Phe Lys Val Trp Asn Leu Glu His Glu Phe Thr His Tyr Leu Asp
```

```
                    500                 505                 510
Gly Arg Tyr Asp Met Ala Gly Asp Phe Ala Ala Ser Thr Ala Lys Pro
            515                 520                 525

Thr Val Trp Trp Ile Glu Gly Leu Ala Glu Tyr Leu Ser Arg Lys Asn
            530                 535                 540

Asp Asn Gln Glu Ser Ile Asp Ala Ala Arg Thr Gly Ala Tyr Arg Phe
545                 550                 555                 560

Ser Asp Val Leu Gly Thr Leu Tyr Ser Ser Asp Tyr Val Ala Arg
                565                 570                 575

Ala Tyr Arg Trp Gly Tyr Met Ala Thr Arg Phe Met Phe Glu Arg His
            580                 585                 590

Arg Ala Asp Val Asp Thr Ile Val Ser Arg Phe Arg Val Gly Asp Tyr
            595                 600                 605

Asp Gly Tyr Ala Asn Tyr Val Ala Tyr Ile Gly Asn Arg Tyr Asp Gly
            610                 615                 620

Glu Phe Val Asp Trp Ala Arg Ala Ala Thr Thr Ala Gly Glu Pro Pro
625                 630                 635                 640

Leu Pro Thr Lys Arg
                645

<210> SEQ ID NO 7
<211> LENGTH: 396
<212> TYPE: PRT
<213> ORGANISM: Burkholderia pseudomallei

<400> SEQUENCE: 7

Met Ala Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Ala Thr Val Leu Ser Ala Lys Phe Gly Gly Glu Ala Lys Lys Tyr Asp
        35                  40                  45

Glu Ile Asp Ala Ala Pro Glu Glu Lys Ala Arg Gly Ile Thr Ile Asn
    50                  55                  60

Thr Ala His Ile Glu Tyr Glu Thr Ala Asn Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Cys Ser Ala Ala Asp Gly Pro
            100                 105                 110

Met Pro Gln Thr Arg Glu His Ile Leu Leu Ala Arg Gln Val Gly Val
        115                 120                 125

Pro Tyr Ile Ile Val Phe Leu Asn Lys Cys Asp Met Val Asp Asp Ala
    130                 135                 140

Glu Leu Leu Glu Leu Val Glu Met Glu Val Arg Glu Leu Leu Ser Lys
145                 150                 155                 160

Tyr Asp Phe Pro Gly Asp Thr Pro Ile Ile Lys Gly Ser Ala Lys
                165                 170                 175

Leu Ala Leu Glu Gly Asp Lys Gly Glu Leu Gly Glu Val Ala Ile Met
            180                 185                 190

Asn Leu Ala Asp Ala Leu Asp Thr Tyr Ile Pro Thr Pro Glu Arg Ala
        195                 200                 205

Val Asp Gly Ala Phe Leu Met Pro Val Glu Asp Val Phe Ser Ile Ser
    210                 215                 220
```

```
Gly Arg Gly Thr Val Val Thr Gly Arg Val Glu Arg Gly Val Ile Lys
225                 230                 235                 240

Val Gly Glu Glu Ile Glu Ile Val Gly Ile Lys Ala Thr Ala Lys Thr
                245                 250                 255

Thr Cys Thr Gly Val Glu Met Phe Arg Lys Leu Leu Asp Gln Gly Gln
                260                 265                 270

Ala Gly Asp Asn Val Gly Ile Leu Leu Arg Gly Thr Lys Arg Glu Asp
            275                 280                 285

Val Glu Arg Gly Gln Val Leu Ala Lys Pro Gly Ser Ile Thr Pro His
        290                 295                 300

Thr His Phe Thr Ala Glu Val Tyr Val Leu Ser Lys Asp Glu Gly Gly
305                 310                 315                 320

Arg His Thr Pro Phe Phe Asn Asn Tyr Arg Pro Gln Phe Tyr Phe Arg
                325                 330                 335

Thr Thr Asp Val Thr Gly Ser Ile Glu Leu Pro Lys Asp Lys Glu Met
                340                 345                 350

Val Met Pro Gly Asp Asn Val Ser Ile Thr Val Lys Leu Ile Ala Pro
            355                 360                 365

Ile Ala Met Glu Glu Gly Leu Arg Phe Ala Ile Arg Glu Gly Gly Arg
370                 375                 380

Thr Val Gly Ala Gly Val Val Ala Lys Ile Ile Glu
385                 390                 395

<210> SEQ ID NO 8
<211> LENGTH: 507
<212> TYPE: PRT
<213> ORGANISM: Burkholderia pseudomallei

<400> SEQUENCE: 8

Met Ala Ile Thr Gln Thr Gly Thr Ser Gln Ser Asp Val Trp Ser
1               5                   10                  15

Gln Ile Gln Asp Ala Ala Gln Ser Leu Ile Asn Gly Ala Thr Gly Lys
                20                  25                  30

Thr Ser Met Asp Val Ser Gly Leu Val Ser Val Leu Val Asn Ala Lys
            35                  40                  45

Thr Ala Gly Gln Ala Ala Glu Ile Lys Asn Gln Ala Ala Trp Asn Ser
50                  55                  60

Thr Gln Ile Ser Ala Leu Gly Ala Leu Lys Leu Ala Leu Ser Asn Leu
65                  70                  75                  80

Lys Thr Gly Val Glu Pro Leu Ser Asp Gly Thr Phe Ala Gln Lys Phe
                85                  90                  95

Thr Ser Lys Ala Ser Gly Lys Gly Leu Gly Ala Thr Met Asp Lys Gly
                100                 105                 110

Thr Val Ala Gly Ser Tyr Gln Val Glu Val Lys Gln Val Ala Arg Ser
            115                 120                 125

Gln Thr Leu Val Ser Ala Gly Phe Asp Pro Lys His Thr Leu Gly Ser
        130                 135                 140

Gly Thr Leu Thr Leu Lys Leu Gly Asp Arg Ser Thr Ser Ile Asp Ile
145                 150                 155                 160

Asp Ala Thr Asn Asn Thr Pro Ala Gly Ile Ala Ala Ile Asn Ser
                165                 170                 175

Ala Lys Asn Asn Pro Gly Val Thr Ala Thr Val Val Thr Gly Thr Asp
            180                 185                 190

Gly Ala His Leu Val Leu Arg Ser Thr Ala Ser Gly Ser Ala Asn Val
        195                 200                 205
```

```
Ile Ser Met Ser Val Ser Asn Leu Lys Asp Asp Ala Gly Leu Ser Gly
    210                 215                 220

Leu Ala Val Gln Ser Thr Ala Asp Asp Lys Gly Lys Ser Ala Ile
225                 230                 235                 240

Thr Ser Ala Gly Asp Ala Trp Lys Gln Ser Asp Phe Ala Gln Asp Ala
                245                 250                 255

Ile Val Thr Val Gly Val Ile Thr Ala Arg Ser Ala Asp Asn Ala
                260                 265                 270

Val Lys Gly Val Ile Ala Gly Val Thr Ile Asn Val Thr Glu Glu Ala
                275                 280                 285

Ile Gly Ala Pro Gln Thr Leu Ser Ile Ala Arg Asp Ile Asp Gly Gln
                290                 295                 300

Ala Arg Ala Val Thr Asn Phe Val Asp Leu Tyr Asn Ser Met Ile Gly
305                 310                 315                 320

Thr Met Ala Gln Leu Thr Ser Phe Asp Lys Thr Ala Lys Pro Gly Gln
                325                 330                 335

Gln Gly Gly Pro Met Ile Gly Asp Ser Met Leu Asn Gly Ile Arg Asn
                340                 345                 350

Ser Leu Ala His Ile Val Gly Gly Val Pro His Gly Glu Asn Lys
                355                 360                 365

Arg Ala Ser Leu Ala Ala Leu Gly Ile Thr Phe Ala Arg Pro Gly Asp
370                 375                 380

Lys Gln Pro Glu Gly Ser Leu Ile Val Asp Lys Ala Lys Leu Asn Glu
385                 390                 395                 400

Ala Leu Gln Asn Asp Pro Gln Ala Val Glu Ala Leu Phe Asn Lys Thr
                405                 410                 415

Asn Gly Ile Gly Thr Gln Ile Thr Lys Ala Leu Asp Val His Leu Arg
                420                 425                 430

Lys Asp Gly Ser Phe Asp Val Arg Ser Asn Ala Ile Asp Arg Asp Met
                435                 440                 445

Lys Ser Ile Ala Gln Arg Gln Ala Arg Leu Glu Thr Tyr Ala Ser Gln
                450                 455                 460

Leu Thr Ala Gln Tyr Lys Ala Gln Phe Thr Ala Leu Asp Ala Leu Met
465                 470                 475                 480

Ala Arg Met Gln Gln Asn Thr Asn Tyr Leu Thr Gln Leu Phe Gly Gly
                485                 490                 495

Ala Asn Ser Ser Gly Ala Leu Ala Asn Asn Lys
                500                 505

<210> SEQ ID NO 9
<211> LENGTH: 567
<212> TYPE: PRT
<213> ORGANISM: Burkholderia pseudomallei

<400> SEQUENCE: 9

Met Gln Thr Ser Arg Lys Ala Leu Pro Leu Ala Leu Gly Leu Ala Ile
1               5                   10                  15

Gly Leu Gly Ala Ala Leu Pro Ala Trp Ala Asp Ser Lys Ala Pro Ser
                20                  25                  30

Pro Gln Glu Glu Ser Arg Arg Ala Ser Leu Thr Arg Gly Val Val Ala
                35                  40                  45

Pro Ala Glu Gln Ala Gly Lys Thr Gly Gln Phe Arg Pro Gly Ala Val
50                  55                  60

Ala Val Thr Leu Ala Ser Pro Ala Phe His Ala Lys Lys Ala Asp Ala
```

```
                65                  70                  75                  80
Ala Ala Met Ala Arg Glu Tyr Val Thr Ala Arg Ala Ala Gln Leu Gly
                85                  90                  95

Leu Asp Lys Ala Ala Leu Ala Asn Leu Val Val Ala Ser Glu Arg Ala
            100                 105                 110

Asp Ala Ala Phe Thr Val Val Arg Phe Gln Gln Arg Ala Ala Gly Leu
            115                 120                 125

Pro Val Tyr Asp Ser Asp Ile Ala Val Thr Val Ala Pro Asp Gly Arg
        130                 135                 140

Val Leu Tyr Val Ala Ser Lys Ala Val Ser Gly Val Ala Ala Val Ser
145                 150                 155                 160

Ser Lys Thr Gln Ala Val Asp Glu Gln Gln Ala Leu Asp Arg Ala Arg
                165                 170                 175

Ala Tyr Leu Gly Val Gly Gly Phe Val Asn Val Gln Ser Gln Leu Val
            180                 185                 190

Ala Phe Val Asp Gly Ala Gly Thr His Thr Ala Trp Lys Val Ser Gly
            195                 200                 205

Arg Pro Gln Asp Ser Leu His Gly Asp Trp Glu Leu Ile Ile Asp Ala
        210                 215                 220

Gly Ser Gly Glu Val Leu Arg Ala Gln Asp Lys Ala Ser Tyr Ala Thr
225                 230                 235                 240

Asp Gly Ser Gly Leu Val Phe Arg Pro Asp Pro Leu Ser Pro Thr Lys
                245                 250                 255

Ser Ser Tyr Gly Ser Pro Gly Phe Lys Asp Asn Asn Asp Ala Asp Ser
            260                 265                 270

Pro Gln Leu Ser Ala Ala Arg Val Arg Val Thr Leu Lys Asp Leu Thr
            275                 280                 285

Gln Thr Ser Gly Gly Tyr Lys Leu Ser Gly Pro Tyr Ala Ser Cys Ile
        290                 295                 300

Asp Phe Asp Ala Pro Leu Asp Lys Ala Cys Pro Val Gln Ala Ser Thr
305                 310                 315                 320

Thr Phe Asp Phe Thr Arg Ser Asn Leu Tyr Phe Glu Ala Val Asn Ala
                325                 330                 335

Tyr Tyr His Ile Asp Thr Phe Leu Arg Tyr Val Asn Leu Thr Leu Gly
            340                 345                 350

Ile Lys Ala Leu Pro Tyr Gln Tyr Ala Gly Gly Val Gln Tyr Asp Pro
            355                 360                 365

His Gly Gln Ser Gly Asp Asp Asn Ser Ser Tyr Ser Pro Ser Ser Gly
        370                 375                 380

Arg Leu Ser Phe Gly Gln Gly Val Asp Asp Ala Glu Asp Ala Asp
385                 390                 395                 400

Val Val Ile His Glu Leu Gly His Gly Ile His Asp Trp Ile Thr Asn
                405                 410                 415

Gly Gly Leu Ser Gln Val Glu Gly Leu Ser Glu Gly Thr Gly Asp Tyr
            420                 425                 430

Leu Ala Ala Ala Tyr Ser Arg Asp Phe Asn Gln Trp Ser Pro Ser Asp
            435                 440                 445

Ala Gln Tyr His Trp Val Phe Asn Trp Asp Gly His Asn Glu Phe Trp
        450                 455                 460

Ala Gly Arg Val Thr Asn Tyr Asn Val Gly Arg Thr Tyr Ala Gln Ile
465                 470                 475                 480

Arg Asn Ala Ala Ile His Thr Ala Gly Gln Tyr Trp Ala Ser Cys Asn
                485                 490                 495
```

```
Met Val Ala Arg Asp Ala Ile Gly Gly Ala Ala Met Asp Lys Ala Phe
                500                 505                 510

Leu Lys Gly Leu Ser Met Thr Asn Gly Ser Thr Asn Gln Lys Ala Ala
            515                 520                 525

Ala Gln Ala Val Leu Thr Ala Ala Ala Leu Gly Tyr Ser Ser Ala
        530                 535                 540

Gln Leu Asn Ala Ile Gly Asp Ala Tyr Asn Lys Ser Cys Thr Tyr Gly
545                 550                 555                 560

Val Thr Val Pro Gln Lys Leu
                565

<210> SEQ ID NO 10
<211> LENGTH: 546
<212> TYPE: PRT
<213> ORGANISM: Burkholderia pseudomallei

<400> SEQUENCE: 10

Met Ala Ala Lys Asp Val Val Phe Gly Asp Ser Ala Arg Ala Lys Met
1               5                   10                  15

Val Glu Gly Val Asn Ile Leu Ala Asn Ala Val Lys Val Thr Leu Gly
            20                  25                  30

Pro Lys Gly Arg Asn Val Val Leu Glu Arg Ser Phe Gly Gly Pro Thr
        35                  40                  45

Val Thr Lys Asp Gly Val Ser Val Ala Lys Glu Ile Glu Leu Lys Asp
    50                  55                  60

Lys Leu Gln Asn Met Gly Ala Gln Met Val Lys Glu Val Ala Ser Lys
65                  70                  75                  80

Thr Ser Asp Asn Ala Gly Asp Gly Thr Thr Thr Ala Thr Val Leu Ala
                85                  90                  95

Gln Ser Ile Val Arg Glu Gly Met Lys Tyr Val Ala Ser Gly Met Asn
            100                 105                 110

Pro Met Asp Leu Lys Arg Gly Ile Asp Lys Ala Val Ala Ala Ala Val
        115                 120                 125

Glu Glu Leu Lys Lys Ile Ser Lys Pro Cys Thr Thr Asn Lys Glu Ile
130                 135                 140

Ala Gln Val Gly Ala Ile Ser Ala Asn Ser Asp Ser Ser Ile Gly Asp
145                 150                 155                 160

Arg Ile Ala Glu Ala Met Asp Lys Val Gly Lys Glu Gly Val Ile Thr
                165                 170                 175

Val Glu Asp Gly Lys Ser Leu Ala Asp Glu Leu Asp Val Val Glu Gly
            180                 185                 190

Met Gln Phe Asp Arg Gly Tyr Leu Ser Pro Tyr Phe Ile Asn Asn Pro
        195                 200                 205

Asp Lys Gln Val Ala Val Leu Glu Asn Pro Phe Val Leu Leu His Asp
    210                 215                 220

Lys Lys Val Ser Asn Ile Arg Asp Leu Leu Pro Val Leu Glu Gln Val
225                 230                 235                 240

Ala Lys Ala Gly Arg Pro Leu Leu Ile Ile Ala Glu Asp Val Glu Gly
                245                 250                 255

Glu Ala Leu Ala Thr Leu Val Val Asn Asn Ile Arg Gly Ile Leu Lys
            260                 265                 270

Thr Val Ala Val Lys Ala Pro Gly Phe Gly Asp Arg Arg Lys Ala Met
        275                 280                 285

Leu Glu Asp Ile Ala Ile Leu Thr Gly Gly Gln Val Ile Ala Glu Glu
```

```
        290                 295                 300
Thr Gly Leu Thr Leu Glu Lys Ala Thr Leu Ala Glu Leu Gly Gln Ala
305                 310                 315                 320

Lys Arg Ile Glu Val Gly Lys Glu Asn Thr Thr Ile Ile Asp Gly Ala
                325                 330                 335

Gly Glu Ala Val Asn Ile Glu Ala Arg Val Lys Gln Ile Arg Thr Gln
                340                 345                 350

Ile Glu Glu Ala Thr Ser Asp Tyr Asp Arg Glu Lys Leu Gln Glu Arg
                355                 360                 365

Val Ala Lys Leu Ala Gly Gly Val Ala Val Ile Lys Val Gly Ala Ala
                370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Ile Val Pro Gly Gly Gly
                405                 410                 415

Val Ala Leu Ile Arg Ala Arg Thr Ala Ile Ala Gly Leu Thr Gly Val
                420                 425                 430

Asn Ala Asp Gln Asn Ala Gly Ile Lys Ile Val Leu Arg Ala Met Glu
                435                 440                 445

Glu Pro Leu Arg Gln Ile Val Thr Asn Gly Gly Glu Glu Ala Ser Val
                450                 455                 460

Val Val Ala Ala Val Ala Ala Gly Lys Gly Asn Tyr Gly Tyr Asn Ala
465                 470                 475                 480

Ala Thr Gly Glu Tyr Val Asp Met Val Glu Ala Gly Val Val Asp Pro
                485                 490                 495

Thr Lys Val Thr Arg Thr Ala Leu Gln Asn Ala Ala Ser Val Ala Gly
                500                 505                 510

Leu Leu Leu Thr Thr Asp Ala Ala Val Ala Glu Leu Pro Lys Glu Asp
                515                 520                 525

Ala Pro Met Pro Gly Gly Met Pro Gly Gly Met Gly Gly Met Gly Met
                530                 535                 540

Asp Met
545

<210> SEQ ID NO 11
<211> LENGTH: 466
<212> TYPE: PRT
<213> ORGANISM: Burkholderia pseudomallei

<400> SEQUENCE: 11

Met Lys Lys Leu Lys Tyr Ala Ala Ala Leu Leu Thr Ala Val Ala Met
1               5                   10                  15

Ser Pro Ser Trp Ser Gln Ala Ser Thr Leu Val Ala Gln Ser His Val
                20                  25                  30

Asp Gly Val Ser Arg Ala Glu Pro Ala Lys Ile Gly Glu Gln Leu Ala
                35                  40                  45

Ala Arg Arg Ala Ser Leu Pro Thr Leu Pro Arg Leu Pro Thr Leu
                50                  55                  60

Ser Ala Gly Ala Ile Arg Gln Ala Gly Leu Arg Ala Pro Leu Ala Lys
65                  70                  75                  80

Arg Gln Ala Thr Leu Ala Ala Pro Ala Ala Thr Val Ala Pro Pro
                85                  90                  95

Val Ala Asn Cys Thr Asp Val Thr Ile Gly Ala Ala Tyr Asn Ala Ala
                100                 105                 110
```

-continued

Thr Ala Pro Ala Gly Gln Ala Asp Cys Phe Gln Phe Val Ala Pro Ser
            115                 120                 125

Ala Thr Lys Ile Val Ala Tyr Val Val Asn Leu Pro Ala Asn Glu Gln
130                 135                 140

His Asp Ala His Leu Val Gln Val Asn Glu Asp Gly Ser Trp Thr Val
145                 150                 155                 160

Leu Asp Ser Gln Ala Asp Leu Ser Pro Asn Lys Ile Val Glu Ala Val
                165                 170                 175

Pro Asn Gly Pro Val Arg Leu Leu Leu Val Ser Ala Gln Gln Gly
            180                 185                 190

Ala Gly Asn Ala Pro Phe Gln Phe Gln Val Leu Gly Thr Thr Gly Tyr
        195                 200                 205

Asp Ser Tyr Glu Pro Asn Asp Ser Ile Leu His Pro Thr Lys Leu Thr
    210                 215                 220

Gly Asn Gln Leu Ile Ser Ala Asn Leu Asp Thr Val Ala Asp Phe Asp
225                 230                 235                 240

Tyr Tyr Ala Val Gln Val Pro Ser Thr Gln Thr Ala Asn Tyr Val Thr
                245                 250                 255

Phe Lys Gly Ala Gly Thr Gln Thr Ala Glu Leu Glu Thr Ala Pro Asn
            260                 265                 270

Thr Trp Ala Thr Leu Ala Ser Gly Thr Ser Tyr Asn Ile Thr Ser Pro
        275                 280                 285

Ala Gly Ala Thr Leu Met Phe Arg Val Tyr Asp Lys Gly Thr Thr Ala
    290                 295                 300

Pro Ala Gln Ala Tyr Thr Leu Arg Ile Ser Asp Gly Ala Gly Thr
305                 310                 315                 320

Ala Gly Phe Tyr Arg Phe Leu Asp Glu Glu Asn Ile Thr His Leu Val
                325                 330                 335

Arg Gly Asn Glu Asn Val Ala Arg Val Val Ser Ala Gly Thr Ile Ala
            340                 345                 350

Trp Asp Ser Thr Gly Asn Val Arg Leu Pro Pro Gly Glu Arg Ile Trp
        355                 360                 365

Leu Arg Ala Tyr Asp Ser Ala Gly Pro Asn Gly Pro Asn Thr Leu Leu
    370                 375                 380

Ser Glu Thr Ser Gly Tyr Thr Asp Ala Asn Gly Asn Leu Leu Val Asn
385                 390                 395                 400

Leu Asn Val Gly Val Cys Gln Gly Gly Gly Thr Met Thr Gly Asp Phe
                405                 410                 415

Asn Thr Met Ser Val Pro Ser Asp Arg Trp Arg Ile Thr Tyr Asn Pro
            420                 425                 430

Tyr Ala Phe Val Val Ala Tyr Leu Asp Asn Ala Gln Ile Arg Ala Gln
        435                 440                 445

Thr Ser Ile Lys His Phe Thr His Ile Cys Thr Glu Gln Tyr Leu Gly
    450                 455                 460

Arg Lys
465

<210> SEQ ID NO 12
<211> LENGTH: 132
<212> TYPE: PRT
<213> ORGANISM: Burkholderia pseudomallei

<400> SEQUENCE: 12

Met Arg Thr Lys Ile Ala Ala Ala Trp Leu Ala Ala Leu Val Pro Phe
1               5                   10                  15

```
Ala Ser Leu Ala Ser Thr Ser Ile Gln Ile Asp Ala Arg Gln Asn Cys
        20                  25                  30

Leu Ala Val Phe Gly Lys Val Ser Gly Ala Ser Ala Thr Phe Gln
            35                  40                  45

Leu Ala Pro Gly Arg Tyr Val Val Ser Ile Ala Ser Asn Asn Met Ser
        50                  55                  60

Cys Ser Gly Gly Ser Leu Thr Asn Gly Cys Leu Ile Asp Thr Val Ile
65                  70                  75                  80

Leu Gln Gly Gly Asn Gly Asn Ser His Trp Gly Val Ala Ile Lys Arg
                85                  90                  95

Pro Thr Val Val Asp Ile Pro Asp Thr Ser Leu Leu Phe Ala Tyr Val
                100                 105                 110

Ser Asp Asp Val Cys Ser Asp Asn Thr Gly Gln Ala Thr Leu Leu Ile
            115                 120                 125

Gln Thr Ala Tyr
    130

<210> SEQ ID NO 13
<211> LENGTH: 10
<212> TYPE: PRT
<213> ORGANISM: Burkholderia pseudomallei

<400> SEQUENCE: 13

Ala Phe Val Glu Pro Gly Ile Ala Pro Arg
1               5                   10

<210> SEQ ID NO 14
<211> LENGTH: 10
<212> TYPE: PRT
<213> ORGANISM: Burkholderia pseudomallei

<400> SEQUENCE: 14

Ala Ser Gly Phe Pro Trp Val Ala Ala Arg
1               5                   10

<210> SEQ ID NO 15
<211> LENGTH: 10
<212> TYPE: PRT
<213> ORGANISM: Burkholderia pseudomallei

<400> SEQUENCE: 15

Thr Gly Asp Ala Val Leu Tyr Ser Tyr Trp
1               5                   10

<210> SEQ ID NO 16
<211> LENGTH: 10
<212> TYPE: PRT
<213> ORGANISM: Burkholderia pseudomallei

<400> SEQUENCE: 16

Val Thr Gly Thr Val Val Thr Ser Pro Lys
1               5                   10

<210> SEQ ID NO 17
<211> LENGTH: 10
```

```
<212> TYPE: PRT
<213> ORGANISM: Burkholderia pseudomallei

<400> SEQUENCE: 17

Ser Ala Trp Ser His Pro Gln Phe Glu Lys
1               5                   10
```

BIOMARKERS FOR DETECTION OF BURKHOLDERIA PSEUDOMALLEI

FEDERALLY-SPONSORED RESEARCH AND DEVELOPMENT

This invention was made with Government support under contract no. HHSO100201500032C awarded by the Department of Health and Human Services (DHHS); Office of the Assistant Secretary for Preparedness and Response; Biomedical Advanced Research and Development Authority (BARDA). The Government has certain rights in this invention.

INCORPORATION-BY-REFERENCE OF MATERIAL SUBMITTED ELECTRONICALLY

Incorporated by reference in its entirety is a computer-readable amino acid sequence listing submitted concurrently herewith, and identified as follows: One 43,762 Byte ASCII (Text) file named "S1647.111.102_Sequence" and created on Mar. 11, 2020.

OVERVIEW

Melioidosis is an infectious disease caused by Gram-negative bacterium *Burkholderia pseudomallei* (BP), which is widely found in soil and water throughout tropical and subtropical regions of the world. People can become infected by BP in a variety of ways, through skin contact, through ingestion of contaminated food or water, and through inhalation of bacteria-containing dusts or aerosols. Melioidosis is difficult to diagnose as patients present with non-specific clinical symptoms and the number of bacterial cells in sampled bodily fluids is typically low. BP is also intrinsically resistant to many antibiotics that are used as first-line treatments in common bacterial infections so that, if patients are not correctly diagnosed early enough to initiate prompt treatment with the correct antibiotic therapy, case fatality rates of greater than seventy percent can occur. A new diagnostic test for melioidosis that has good sensitivity, specificity and is able to provide results more rapidly than current, culture-based methods, could save many lives, especially if BP were to be employed as a weapon of bioterrorism.

SUMMARY

Various embodiments in accordance with the present description are directed to sets of biomarkers that are produced by BP and that are released into a body fluid during the course of an infection. Detection of a member of the set of biomarkers in a sample taken from a patient, either directly or when coupled with a short ex vivo incubation period, can be used to diagnose an active case of melioidosis. Also described are reagents kits, apparatuses and methods that can be used in certain embodiments to form a diagnostic test for melioidosis.

Specific embodiments are directed to a set of BP biomarkers that can be used to infer, based on their presence in a test sample from a subject, an infection caused by BP, such as a melioidosis infection. Sensitive detection methodologies can allow for detection of the presence of one or more members of the set of BP biomarkers and the rapid diagnosis of melioidosis within twenty-four hours or less of sampling, and with diagnostic sensitivity greater than approximately sixty percent. In response to detecting an infection caused by BP, the correct lifesaving antibiotic therapy effective against melioidosis can be started for a patient. The detection can be based on a parallel assay for both BP-derived biomarkers and host immunoglobulin (Ig) responses to BP in a sample.

In specific embodiments, the BP biomarkers are among a class of polypeptides or other biomolecules released by the pathogen. The set of BP biomarkers can be derived from molecules used by the organism to establish and maintain an infection, including those involved in evading host defenses, acquiring the necessary nutrients, and disseminating from the initial site of infection during a case of melioidosis. More specifically, the BP biomarkers are associated with a protein (or with a uniquely-determined portion of a protein such as an epitope) or other molecule secreted or otherwise released from BP and are encoded either directly or indirectly in the bacterial genome. The different natural strains of BP have significant amounts of genetic diversity between them. For an efficient diagnostic test, the set of BP biomarkers can come from those that are present in and highly conserved between various strains of BP. As the BP biomarkers are associated with proteins or other molecules released from BP, probing for the presence of BP can occur in samples that contain no bacterial cells and can be more rapid than tests that rely on growing the organism in culture bottles from relatively large volumes of collected patient samples. The BP biomarkers, in accordance with various embodiments, are less dependent on a patient's health status, such as the ability to mount an immune response to the bacteria, than diagnostic attempts using serology, making them more widely useful for diagnosis from blood and/or other types of biological samples. Experimental embodiments demonstrate the detection of the BP biomarkers in vivo. For example, two such BP antigens associated with the BP biomarkers, a chitin-binding protein (BPSS0493) and the protein BPSL1622, are detected in vivo, in various embodiments.

Various specific embodiments are directed to detecting a BP infection in a subject by detecting binding between a set of first agents and one or more of a set of BP biomarkers (which are associated with one or more proteins released from BP cells or proteins that combine with a molecule released from BP cells) in a biological sample taken from the subject.

Example methods can include causing a physical interaction between the biological sample, such as in vitro, and a set of first agents by exposing the set of first agents to the biological sample. The set of first agents are specific to one or more of a set of BP biomarkers associated with one or more proteins released from BP cells or otherwise associated with another molecule released from BP cells. The other molecules, such as lipids, carbohydrates or metabolites released from BP, combine with the one or more proteins which may be present in the sample. The method can further include determining the presence of BP in the biological sample based on detected binding between one or more of the set of first agents and the one or more of the set of BP biomarkers within twenty-four hours of causing the physical interaction, such as between one hour and up to twenty-four hours. In a number of embodiments, the method does not require incubating the biological sample in a culture bottle for a long time period, e.g., greater than one day, and allows for the presence of BP in a patient to be determined in less than twenty-four hours from when the physical interaction occurs between the set of first agents and the biological sample.

In a number of embodiments, the physical interaction is coupled to or includes performing an assay, a secondary assay or other type of test. For example, the physical interaction can be used in performing a number of assays including, but not limited to, immunochromatographic assays such as a lateral flow test, an immune-polymerase chain reaction (PCR) assay, a mass spectrometry assay, testing for presence of BP using an antibody specific to the BP biomarker. Examples include tests such as a BP-specific lateral flow strip, tip or dipstick, BP-specific antigen latex agglutination assays, multiplex enzyme-linked immunosorbent assay (ELISA), latex beads with antibodies attached for agglutination assays, up-converting phosphor particles with attached antibodies for lateral flow assays, other types of assays with antibodies attached to beads, nano-particles, surfaces or capillaries, and magnetic particles with attached affinity reagents.

In specific embodiments, the BP biomarker is associated with at least one protein selected from the group consisting of: a chitin-binding protein (BPSS0493), a protein BPSL1622, a protein BPSL2703, and an exported chitinase protein (BPSL1763), as well as combinations thereof and proteolyzed or biologically modified forms thereof, wherein the genes expressing each of these protein sequences are present in all or nearly all of the strains of BP. For example, one or more of the set of BP biomarkers can be associated with a protein that includes a sequence selected from the group consisting of SEQ ID NOs: 01, 02, 03, 04, 05, 06, 07, 08, 09, 10, 11, and 12, as well as combinations thereof. The set of first agents can be used to form an assay for the one or more of the set of BP biomarkers having an analytical sensitivity to the one or more of the set of BP biomarkers of at least one nanogram/milliliter. Furthermore, the sequences of the proteins for the biomarkers can be highly conserved, as well as being distinct from most other pathogenic bacteria, giving them utility for diagnosing melioidosis. The one or more BP biomarkers can have at least one peptide sequence selected from the group consisting of but not limited to: AFVEPGIAPR (e.g., BP biomarker chitin-binding protein (BPSS0493)), ASGFPWVAAR, TGDAVLYSYWQR, VTGTVVTSPK, SAWSHPQFEK (e.g., hypothetical protein BPSL2703), and combinations thereof and in addition proteolyzed or biologically modified forms thereof. For example, one or more of the BP biomarkers can have a peptide sequence selected from the group consisting of SEQ ID NOs: 13, 14, 15, 16, and 17, as well as combinations thereof. Example biologically modified forms include minor sequence variants such as amino acid substitutions, as may occur or are known to be present in various naturally-occurring strains of BP or which may be introduced by genetic engineering.

Methods, in various specific embodiments, can further be applied to administer an antimicrobial agent to the subject for treating melioidosis in response to determining the presence of BP in the biological sample, such as detecting the presence of one or more members of the set of BP biomarkers in a biological sample obtained from the subject. The antimicrobial agent can be selected from Ceftazidime, Meropenem, Trimethoprim-sulfamethoxazole, Doxycycline, and combination thereof. The application can also be extendable to treatments that may include, for example, targeting of one or more of the set of biomarkers for therapy.

The physical interaction can include one or more of the described assays and/or tests. For example, the physical interaction can further include applying a set of second agents (e.g., a label or a secondary antibody) used to detect the one or more of the set of BP biomarkers in a complex with the set of first agents, as in a sandwich-format assay. In other specific embodiments, the physical interaction can include an antibody test and/or flow assay. For example, causing the physical interaction can include binding the one or more of the set of first agents to the one or more of the set of BP biomarkers and binding one or more of the set of second agents (e.g., detection agents/labels) to the one or more of the set of first agents or an epitope of the one or more proteins. In such embodiments, determining the presence of BP in the biological sample includes identifying the presence of a least a portion of the set of second agents (e.g., the label). In some embodiments, the set of first agents include a first antibody (or other affinity molecule) and the set of second agents include a second (e.g., detection) antibody bound to a label, and the method further includes exposing the biological sample to the second antibody and, therein, binding the second antibody to the protein. In other embodiments, the method further includes exposing the biological sample to the second antibody and, therein, binding the second antibody to the first antibody.

Other example embodiments are directed to a latex agglutination assay. In such embodiments, causing the physical interaction includes exposing the biological sample to a plurality of solid supports (e.g., beads), each of the plurality of solid supports bound to at least one of the set of first agents, and determining the presence of BP in the biological sample includes identifying agglutination of the solid supports.

In various embodiments, the physical interaction occurs between the BP biomarker and an antibody specific to it. For example, the set of first agents include the antibody bound to a label, and causing the physical interaction includes bindings the antibody to the BP biomarker and determining the presence of BP in the biological sample includes determining the physical interaction occurred by identifying the presence of the label. The interaction can be produced by mixing the antibody with the biological sample (e.g., a blood sample), wherein the presence of the BP biomarker within biological sample results in binding of the BP biomarker to the antibody. The antibody can be modified in such a way as to facilitate its detection, such as by being bound to a label. Additionally, a method to detect the interaction between the antibody and a member of the set of BP biomarkers is included. The detection may include the stepwise capturing of the antibody-biomarker complex using a solid-support-bound affinity reagent for the biomarker, washing to remove un-complexed antibody, and adding a reagent to detect the presence of the remaining complexed antibody. The presence of the BP biomarker in the sample can thereby be inferred.

In more specific embodiments, the physical interaction includes forming an assay. The assay design can include a first antibody specific to a first BP biomarker (e.g., a BP biomarker associated with a chitin-binding protein BPSS0493) of the set of BP biomarkers and a second antibody specific to a second BP biomarker of the set of BP biomarkers that is different than the first (e.g., a BP biomarker associated with the protein BPSS1622). Although embodiments are not limited to assays for a disembodied set of two BP biomarkers, and can also include expanded or contracted sets with more or fewer BP biomarkers or targets and the associated specific capture and detection reagents. Further, the sets of first agents and/or second agents may include agents other than antibodies, such as partial antibodies, anti-antibodies, and other compounds having a sequence specific to the BP biomarker, the protein associated with the BP biomarker and/or other compounds (such as the first antibody).

As another specific example, causing the physical reaction includes applying the first antibody to the biological sample. The presence of the BP biomarker within the biological sample causes binding of the first antibody to the BP biomarker. The physical reaction can further include applying a label-containing second antibody to the biological sample, the second antibody being specific to an epitope of the first antibody or an epitope of the protein associated with the BP biomarker. The first and second antibodies can be man-made monoclonal antibodies.

The set of first agents can include a volume of an agent specific to a particular BP biomarker of the set of BP biomarkers. In other examples, the set of first agents includes aliquots of a plurality of different agents, where each of the different agents is specific to the particular BP biomarker with variations. In other examples, the set of first agents includes aliquots of a plurality of different agents, where each of the different agents is specific to a different BP biomarker of the set. Accordingly, various specific embodiments are directed to use of multiple BP biomarkers. For example, the set of first agents includes a first antibody and a second antibody and causing the physical interaction between the biological sample and the set of first agents includes exposing the biological sample to a plurality of antibodies, the plurality of antibodies including the first antibody specific to a first BP biomarker of the set of BP biomarkers associated with a first protein of the one or more proteins and a second antibody specific to a second BP biomarker of the set of BP biomarkers associated a second protein of the one or more proteins. Further embodiments may include binding to more than two different BP biomarkers, such as binding of two to ten or more biomarkers.

The above described methodology may be used to determine of the presence of BP within the biological sample in a time that is less than the subject may pass from a melioidosis infection. For example, the presence of BP is determined between an hour and twenty-four hours from causing the physical interaction. Further, the BP biomarker can have a sensitivity to the first agent of at least sixty percent.

In other specific embodiments, the method further includes determining the presence of BP in the disembodied biological sample by mixing the biological sample with at least one exogenously produced BP biomarker or BP biomarker fragment and identifying specific IgG antibodies present in the sample. For example, determining the presence of BP in the biological sample further includes exposing the set of BP biomarkers to the biological sample and identifying the presence of immunoglobulin molecules reactive with the set of BP biomarkers in the biological sample.

Specific example method embodiments can include determining a presence of BP in a subject by detecting whether any member of the set of BP biomarkers is present in the biological sample. The detection can include contacting the biological sample with a set of first agents specific to the set of BP biomarkers and detecting binding between members of the BP biomarker set and their corresponding specific first agents of the set of first agents, wherein the set of BP biomarkers is comprised of proteins released from BP cells or proteins which combine with other molecules released from BP cells.

A number of embodiments are directed to an antibody or other agent that is developed to be specific to the BP biomarker, such as a man-made monoclonal antibody. An antibody can bind to a BP biomarker associated with at least one protein selected from the group consisting of: a chitin-binding protein (BPSS0493), a protein BPSL1622, a protein BPSL2703, and an exported chitinase protein (BPSL1763), as well as combinations thereof and proteolyzed or biologically modified forms thereof.

More specific embodiments are directed to an apparatus (e.g., an assay consisting of, but not limited to, a lateral flow test) for detecting BP biomarker(s) in a biological sample obtained from a subject to infer the existence of an infection caused by BP, to predict the severity of an infection caused by BP, and/or to monitor the course of the disease during treatment of a patient previously diagnosed as having a BP infection. The apparatus includes the various reagents (including a set of first agents and a set of second agents) and a solid support having a first region, a second region, and a third region. The first region is to receive a biological sample or a diluted form of a biological sample obtained from a subject. The biological sample may not be cultured, in various embodiments, allowing for detection of BP in less time than a melioidosis infection may kill the subject, such as within twenty-four hours of causing the physical interaction between the biological sample and the set of first agents. The second region includes the set of first agents each bound to a label. The set of first agents are adherent on the second region in such a way that the first agents are released into the sample solution during or after application of the sample. For example, upon interaction with the biological sample, the set of first agents are releasable from the second region. The set of first agents are specific to one or more of a set of a BP biomarkers, associated with a protein released by BP cells or associated with other molecules released from BP cells. The third region includes a set of second agents (e.g., capture antibodies) immobilized to the third region and specific to the one or more proteins. The set of first agents or at least one first agent of the set can be specific to a first epitope or region of a respective protein, which includes or is otherwise associated with the BP biomarker, and the set of second agents or at least one of the set is specific to a second epitope or region of the respective protein. In other examples and/or in addition, the set of second agents or at least one of the set may also be specific to the first epitope of the respective protein, such as when the BP biomarker is associated with an epitope that occurs multiple times on the protein.

In response to receipt of the biological sample, the first region is to pass a portion of the biological sample to the second region, the second region is to pass at least some of the portion of the biological sample to the third region. In a specific embodiment, the second region includes a conjugate that includes the set of first agents and a salt-sugar matrix that binds the set of first agents to the second region. The salt-sugar matrix can dissolve in response to the portion of the biological sample passing to the second region, thereby releasing the portion of the set of first agents and allowing for migration to the third region. The presence of the BP biomarker causes accumulation of the label in the third region indicating a presence of BP in the biological sample with twenty-four hours of application of the biological sample. In a number of embodiments, the solid support further includes one or more additional regions containing immobilized control agents that bind to the set of first agents.

Other specific examples are directed to a kit that includes the various reagents and a solid support, such as for forming an assay. The reagents include the set of first agents and a set of labels. Each label can be bound to a respective first agent or the reagents may include a set of second agents bound to the label. The set of first agents are to bind to one or more of a set of BP biomarkers associated with one or more proteins released from BP or associated with other molecules released from BP as present in the biological sample. For example, each of the set of first agents may include a man-made molecule that is designed to bind to the one or more of the set of BP biomarkers. The set of labels can bind to the one or more proteins, which may include an indirect binding. For example, the label may be bound to a respective first agent or to a respective second agent that binds to either the first agent or the protein, such that binding of the first agent to the BP biomarker or binding of the second agent to the first agent or the protein results in the label being indirectly bound to the protein. The solid support can receive application of a biological sample, the set of first agents and the set of labels, and in response, presence of the BP biomarker causes accumulation of one or more of the sets of labels bound to the solid support and indicates the presence of BP in the biological sample within twenty-four hours of the application of the biological sample. The kit may further include a set of second agents which bind the set of labels to the one or more proteins and the solid support is to further receive application of the set of second agents. The set of second agents can bind to the set of labels to the one or more proteins, such as by binding directly to a respective protein or by binding to a particular first agent and thereby binding the label to the protein.

In various embodiments, the application of the sample can include immobilizing the biological sample to the solid support, exposing the solid support with the immobilized biological sample to a volume of the first set of agents bound to the label, and washing away unbound first agents. In other embodiments, the application can include immobilizing the volume of the set of first agents or a volume of each of a plurality of different first agents of the set, exposing the solid support with the immobilized first agents to the biological sample, washing away unbound biological sample, exposing the solid support to a volume of a set of second agents (e.g., detection antibody bound to the label), and washing away unbound second agents. The second agents can bind to respective complementary first agents, a repetition of the BP biomarker, and/or another epitope of the protein associated with the BP biomarker.

The diagnostic information from a positive test for one or more of the set of BP biomarkers can be used to identify a drug for use in treating a melioidosis infection in a subject. The process consists of assaying a biological sample from the subject, determining if the biological sample has a presence of one or more of a set of BP biomarkers, interpreting whether, e.g., the biomarker presence or an absolute or relative quantitative amount indicates a (preferred) drug and administering in an optimal delivery form a therapeutically effective amount of a drug to the subject in response to the BP biomarker being present. The BP biomarker is associated with at least one protein selected from the group consisting of a chitin-binding protein (BPSS0493), a protein BPSL1622, a protein BPSL2703, and an exported chitinase protein (BPSL1763) among others in a list of proteins released by BP into circulation, such as Table 1 listed herein. The drug includes an antimicrobial agent effective against melioidosis and selected from Ceftazidime, Meropenem, Trimethoprim-sulfamethoxazole, Doxycycline, and combinations thereof.

Various embodiments are directed to methods for treating a melioidosis infection in a subject. The method includes assaying a biological sample from the subject, determining if the biological sample has a presence of a BP biomarker based on the assay. The BP biomarker can be associated with at least one protein selected from the group consisting of a chitin-binding protein (BPSS0493), a protein BPSL1622, a protein BPSL2703, and an exported chitinase protein (BPSL1763), as well as combinations thereof and proteolyzed or biologically modified forms thereof. The method further includes administering a therapeutically effective amount of a compound to the subject for the treatment of melioidosis infection in response to determining the BP biomarker is present. The compound includes an antimicrobial agent selected from Ceftazidime, Meropenem, Trimethoprim-sulfamethoxazole, Doxycycline, and combination thereof. The assay can include any of the above described assay techniques.

The above overview is not intended to exhaustively describe each illustrated embodiment or every implementation of the present disclosure. The figures and detailed descriptions that follow exemplify, more particularly, these embodiments.

BRIEF DESCRIPTION OF THE DRAWINGS

Various exemplary embodiments are understood by considering the following detailed descriptions in connection with the accompanying drawings, in which:

FIG. 1 illustrates an example method for determining a presence of BP in a biological sample, in accordance with various embodiments;

FIG. 2 illustrates an example method for determining a presence of BP in a biological sample and revising treatment of a patient, in accordance with various embodiments;

FIGS. 3A-3C illustrate example solid supports for determining a presence of one or more of a set of BP biomarkers or the presence of antibody responses against the one or more BP biomarkers, in accordance with various embodiments;

FIGS. 4A-4B illustrate example assays for determining a presence of one or more of a set of BP biomarkers, in accordance with various embodiments;

FIG. 5 is a schematic of an example protocol for in vivo detection of the chitin-binding protein by LC-MS/MS, in accordance with various embodiments;

FIG. 6 illustrates representative LC-MS/MS data for detecting a tryptic peptide derived from the chitin-binding protein captured from a BP-infected NHP serum sample collected at the terminal bleed, in accordance with various embodiments;

FIG. 7 is a schematic of an example ELISA assay for characterizing the BP chitin-binding protein and identifying candidate panels for clinical diagnosis of melioidosis, in accordance with various embodiments;

FIGS. 8A-8D illustrate example ELISA results for the detection of BP chitin-binding protein biomarkers in BP-infected NHPs, in accordance with various embodiments;

FIG. 9 is a schematic of an example ELISA assay for characterizing BPSL1622 and identifying candidate panels for clinical diagnosis of melioidosis, in accordance with various embodiments;

FIGS. 10A-10D illustrate example results for the detection of the BPSL1622 by ELISA in BP-infected NHPs, in accordance with various embodiments;

FIG. 11 is a schematic of an ELISA method for detecting IgG host-response to the BP antigens in accordance with various embodiments;

FIGS. 12A-12B illustrate an example of time profiles of IgG antibody response to the BP antigen, chitin-binding protein in BP-infected NHPs, in accordance with various embodiments;

FIGS. 13A-13B illustrate an example of time profiles of IgG antibody response to the BP antigen, exported chitinase in BP-infected NHPs, in accordance with various embodiments;

FIGS. 14A-14B illustrate an example time profile of IgG antibody response to the BP antigen, antigen, the protein BPSL2703, in accordance with various embodiments; and FIG. 15 illustrates a schematic example showing diagnostic sensitivity, in various embodiments, can be maximized by combining a plurality of the BP biomarkers with the host immune-response detection.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are applicable to a variety of different types of methods, systems and arrangements for detecting *Burkholderia pseudomallei* (BP) in a subject from testing a corresponding biological sample. A presence of BP in the subject is determined, in some embodiments, by detecting the presence of one or more of the set of BP biomarkers, which are associated with proteins released from BP cells and/or proteins that combine with other molecules released from BP cells, in the biological sample. While the present disclosure is not necessarily limited to such applications, various aspects of the disclosure may be appreciated through a discussion of various examples using this context.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Various embodiments are directed to BP biomarkers that are associated with proteins released from or secreted by BP and/or proteins that combine with other molecules released from or secreted by BP. Example molecules include proteins, lipids, carbohydrates, and metabolites which are released from BP cells, such as in the form of vesicles, and that combine with proteins present in the sample. The BP biomarkers can be used for detection of a presence of BP in a biological sample. As the proteins or other molecules are released from BP, the BP biomarkers can be detected in a biological sample using methods that are culture independent (e.g., do not necessarily rely on or include culturing of the sample), and which can reduce the time for detection. For example, microbiological culturing of samples takes forty-eight to seventy-two hours to diagnose, while diagnosis of melioidosis with the BP biomarkers can occur in less than twenty-four hours. As melioidosis often kills its host within twenty-four to forty-eight hours of the host exhibiting symptoms, detection times of less than twenty-four hours is vital for providing life-saving treatment. The low levels of circulating bacterial cells in melioidosis results in a diagnostic delay for microbiological culturing of not typically longer than seventy-two hours while detection of proteins released as many copies per cell into circulation is capable of achieving an improvement for a sampling to result time less than one hour. For example, in an experimental test, positive diagnostic test were obtained for four out of the five patients using ELISA assays probing two biomarkers consisting of a chitin-binding protein (BPSS0493) and a protein BPSL1622, where the results were obtained in some instances in less than twelve hours, in other instances, less than six hours, and, in yet other instances, results can be obtained in less than one hour.

Increasing the difficulty in treating melioidosis is the fact that first-line antibiotics, often given to patients when diagnosis cannot be made and in hopes of seeing positive results, are ineffective. Various specific embodiments can include the detection of one or more of the set of BP biomarkers and, responsive thereto, the treatment for the subject can be adjusted including administering an antimicrobial agent to the subject for treating melioidosis. The antimicrobial agent can include Ceftazidime, Meropenem, Trimethoprim-sulfamethoxazole, and/or Doxycycline, among other antimicrobial agents that are effective in treating melioidosis.

The BP biomarkers are associated with a set of proteins released from or secreted by BP and/or proteins which combine with other molecules released from or secreted by BP. The set of proteins can include a chitin-binding protein BPSS0493, a protein BPSL1622, a protein BPSL2703, and an exported chitinase protein BPLS1763, among other biomarkers such as those listed in Tables 1-4 below and as well as proteolyzed or biologically modified forms thereof. The BP biomarkers can be associated with proteins having an amino acid sequence selected from SEQ ID NOs: 01-12, in specific examples, such as various combinations of SEQ ID NOs: 01-12. The BP biomarker(s) can be detected by performing a variety of tests, such as an immunochromatographic strip assay (lateral flow strip) or other lateral flow test, polymerase chain reaction (PCR) assay, testing for presence of BP using an antibody specific to one or more of the set of BP biomarkers, liquid chromatography tandem mass spectrometry (LC-MS/MS), BP-specific antigen latex agglutination assays, multiplex ELISA, antibody coated latex agglutination assays, antibody coated up-converting phosphors for lateral flow assays, antibody coated bead assays, and affinity reagent coated magnetic particles.

Turning now to the figures, FIG. 1 illustrates an example method for determining a presence of BP in a biological sample, in accordance with various embodiments. The presence of BP can be determined using an apparatus and/or kit. The apparatus can include hardware components for performing a photometric scan combined with processing circuitry to digitize detector signals for software analysis, although embodiments are not so limited. For example, apparatuses and/or kits can include reagents and a solid support for forming an assay. The assays can be used to test for the presence of BP in a biological sample without the use of optical scanning and/or processing circuitry, such as a color-indicating, visibly-readable lateral flow test.

As illustrated, a biological sample 103 is obtained from a subject such as a human 101. Although the embodiment illustrates a blood sample being obtained directly from a human 101, embodiments are not so limited and the blood sample may be previously obtained and/or may be obtained from other organisms and used to identify antibodies to treat the particular organism (e.g., other vertebrates, such as horses, goats, sheep, dogs, pigs, cats, cattle, rodents, reptiles, fish, and birds). The biological sample 103 can include urine, sputum, pus, saliva, cerebrospinal fluid samples or other types of samples. A set of first agents are exposed to the biological sample 103, at 104. Exposing the set of first agents to the biological sample 103 may cause a physical interaction between the sample 103 and one or more of the set of first agents.

The set of first agents are specific to one or more of a set of BP biomarkers associated with one or more proteins released from BP or associated with another molecule released from BP. A protein that is associated with another molecule may combine or bind with the other molecule. Example molecules released from BP include proteins, lipids, carbohydrates, and metabolites, some of which may be released in the form of vesicles. The set of first agents can be used to form an assay for the one or more of the set of BP biomarkers having an analytical sensitivity in the biological sample of at least one nanogram/milliliter. The set of first agents may include antibodies that bind specifically (e.g., with high affinity) to the one or more of the set of BP biomarkers. In a number of embodiments, the antibodies are immobilized on or irreversibly conjugated to a solid support (e.g., a substrate), such as a glass slide or plastic microtiter plates. In other embodiments, the biological sample 103 is immobilized to the solid support or substrate and exposed to the antibodies. Biological samples that exhibit the one or more BP biomarkers can bind to at least a portion of the set of first agents.

In some embodiments, the set of first agents includes a volume of a first agent specific to a particular BP biomarker of the set of BP biomarkers. In other embodiments, the set of first agents includes a volume of a plurality of different first agents, where each of the different first agents is specific to the particular BP biomarker with slight variations. For example, the variations may include sequence variations of the first agents (e.g., affinity molecules) which may exhibit higher affinities to the particular BP biomarker within different subject populations and/or BP strains. In further embodiments, assays and/or tests are directed to use of multiple BP biomarkers. For example, the set of first agents includes aliquots of each of a plurality of different first agents, where each volume of a different first agent is specific to a different BP biomarker of the set. Further embodiments can include assays or test targeting more than two different BP biomarkers, such as targeting two to ten or more biomarkers.

In specific embodiments, the set of BP biomarkers are associated with at least one protein that includes an amino acid sequence selected from the group consisting of: SEQ ID NOs: 01, 02, 03, 04, 05, 06, 07, 08, 09, 10, 11, and 12, as well as combinations thereof and/or proteolyzed or biologically modified forms thereof. Example BP biomarkers include AFVEPGIAPR, ASGFPWVAAR, TGDAVLYSYWQR, VTGTVVTSPK, SAWSHPQFEK, and combinations thereof, which are identified respectively by SEQ ID NOs: 13-17 in the attached sequence listing, although embodiments are not so limited and the BP biomarkers can be associated with a variety of proteins having amino acid sequences that include SEQ ID NOs: 01-12 or are otherwise identified below by Tables 1-4.

As noted above, an assay or test can be directed to combinations of BP biomarkers, such as proteins identified by SEQ ID NOs: 01-12. For example, the set of first agents can be used to form an assay specific to a plurality or all of the set of BP biomarkers, wherein different first agents of the set of first agents are to specifically bind to a respective one of the set of BP biomarkers. As specific examples, the set of first agents can be designed to specifically bind to BP biomarkers associated with different combinations of proteins having amino acid sequences identified by SEQ ID NOs: 01-12, and/or associated with additional proteins, such as those identified below by Tables 1-3. In specific embodiments, the set of first agents are configured to specifically bind to a set of BP biomarkers associated with a plurality of proteins identified by SEQ ID NOs: 01-12. Although embodiments are not so limited and various assays can be formed, such as assays targeting BP biomarkers associated with sub-combinations of the proteins having amino acid sequences identified by SEQ ID NOs: 01-12, e.g., proteins having amino acid sequences identified by SEQ ID NOs 01 and 02, 01 and 03, 01-03, 01 and 04, 01-04, 01-05, 01-03 and 05, etc. The above example combinations and sub-combinations are not intended to be limited, and embodiments are directed to methods of detecting and forming assays directed to BP biomarkers associated with various combinations of proteins as identified by SEQ ID NOs: 01-12 as well as additional proteins identified in Tables 1-3 below.

In some embodiments, the set of first agents are bound to a label which can be detected. In other embodiments, a set of second agents can be applied, which can occur prior to or after exposing the biological sample 103 to the set of first agents. The set of second agents may include a label, such as a fluorescent, enzymatic and/or radioactive label that binds to the one of the set of first agents and/or can include a label containing the second agent, such as a labeled-second antibody that binds to either the respective first agent or another epitope or region associated with the BP biomarker.

Accordingly, the set of first agents may be capture agents and/or detection agents. The agents are man-made affinity molecules with binding specificity to the target molecule or compound. Example agents include an antibody, an anti-antibody, a partial antibody, and other affinity molecules exhibiting complementary sequences to the target molecule or compound. A capture agent includes or refers to an agent that binds to the target molecule or compound and effectively captures the target. A detection agent includes or refers to an agent that binds to the target molecule, compound or a capture agent bound to the target molecule or compound and which includes a label that can be detected.

At 106, binding between one or more of the set of first agents and the one or more of the set of BP biomarkers is detected within twenty-four hours of causing the physical interaction. The binding can be detected using the label, such as a second agent. The detected binding can be interpreted as the presence of BP in the subject (e.g., human 101), at 108. That is, the method can include determining a presence of BP in the biological sample based on detected binding between the one or more of the set of first agents and the one or more of the set of BP biomarkers, and, optionally, without culturing the biological sample. The presence of BP can be inferred by detecting one or more of the set of BP biomarkers, which may include a general presence or a quantitative amount, such as an absolute or relative quantitative amount of the BP biomarker. The presence or quantitative amount of one or more the BP biomarkers can be used to select a therapeutic drug and/or a therapeutically effective amount of the drug for optimal treatment of the subject.

The physical interaction between the set of first agents and biological sample can be performed in variety of ways. In various embodiments, the interaction can include physically mixing the set of first agents and the biological sample 103, or a pre-treated form of the biological sample 103, which initiates an assay and/or other type of test. For example, physical mixing can be part of an immunochromatographic strip assay or other lateral flow test polymerase chain reaction (PCR) assay, testing for presence of BP using an antibody specific to the BP biomarker, LC-MS/MS, including testing such as a BP-specific lateral flow strip, BP-specific antigen latex agglutination assays, multiplex ELISA, antibody coated latex agglutination assays, antibody coated up-converting phosphors for lateral flow assays, antibody coated bead assays, and affinity reagent coated magnetic particles.

As described above, the set of first agents can each include an antibody (or another type of affinity molecule) bound to a label. Causing the physical interaction can include binding one or more of the antibodies to the one or more of the set of BP biomarkers and determining the presence of BP in the biological sample 103 includes determining the physical interaction occurred by identifying the presence of the label after processing. In other embodiments, causing the physical interaction includes binding the one or more of the set of first agents to the one or more of the set of BP biomarkers, and binding one or more of a set of second agents to the one more of the set of first agents or an epitope or other region of the one or more proteins. For example, the second agents may bind to the same BP biomarker, in instances in which the protein includes a plurality of the BP biomarker, or to another epitope or region of the protein. In such embodiments, determining the presence of BP in the biological sample 103 includes identifying the presence of the one or more of the set of second agents (e.g., via the label).

In related specific embodiments, the set of first agents includes first antibodies and the set of second agents includes second antibodies bound to a label (e.g., detection antibodies or labeled anti-antibodies). In such embodiments, the method further includes exposing the biological sample 103 to the second antibodies and, therein, binding one or more of the second antibodies to the one or more proteins. In other embodiments, the method further includes exposing the biological sample 103 to the second antibodies and, therein, binding one or more of the second antibodies to one or more of the first antibodies. Causing the physical reaction may include applying the first antibodies to the biological sample 103 and applying the second antibodies bound to a label to the biological sample 103. The presence of the BP biomarker within biological sample 103 causes binding of the first antibody to the BP biomarker, and the second antibody being specific to an epitope of the first antibody or an epitope of the protein associated with the BP biomarker.

As noted above, specific embodiments are directed to use of multiple BP biomarkers. For example, causing the physical interaction includes exposing the biological sample 103 to the set of first agents, where subsets of first agents of the set are specific to different ones of the set of BP biomarkers. As a specific example, the set of first agents may include a plurality of antibodies. Causing the physical interaction between the biological sample 103 and the set of first agents includes exposing the biological sample to the plurality of antibodies, the plurality of antibodies including a subset or a volume of a first antibody specific to a first BP biomarker of the set and a subset or a volume of a second antibody specific to a second BP biomarker of the set. The first and second BP biomarkers may be associated with different ones of the proteins.

Although the above describes use of antibodies as the set of first agents, embodiments are not so limited and may include a variety of different agents having an affinity to the BP biomarker. Further, although not illustrated, the method can include administering an antimicrobial agent to the subject for treating melioidosis in response to determining the presence of BP in the biological sample 103. Example antimicrobial agents include Ceftazidime, Meropenem, Trimethoprim-sulfamethoxazole, and Doxycycline. Additionally, although not illustrated, determining the presence of BP in the biological sample 103 can further include exposing the set of BP biomarkers to the biological sample 103 and identifying the presence of immunoglobulin molecules reactive with the set of BP biomarkers in the biological sample.

FIG. 2 illustrates an example method for determining a presence of BP in a biological sample and revising treatment of a patient, in accordance with various embodiments. As previously described, a set of first agents are exposed to a biological sample 103, at 210. The biological sample 103, in specific embodiments, is a blood sample of a subject suspected of having, or known to have, melioidosis. The blood sample is obtained from an organism, such as a human 101 as illustrated, although embodiments are not so limited.

The mixing of the biological sample 103, or a pre-treated form of the biological sample 103, with the set of first agents (e.g., antibodies), allows for the physical binding interaction between any of the set of BP biomarkers that may be present in the biological sample 103 and the first agent. The set of first agents can be bound to a solid surface, such as a well of a microtiter plate, a glass slide or a bead, allowing BP biomarkers that have bound to the set of first agents to be removed from the bulk solution, separated and concentrated. In some embodiments, the presence of BP biomarkers is determined by exposing the solid support or substrate (e.g., glass substrate or nanowell array) to a solution containing a set of second agents, such as a set of one or more BP-biomarker specific detection antibodies that are labeled, at 212. The set of second agents each contain a label, such as a fluorescent, enzymatic, or radioactive label or an otherwise detectable molecular tag such as biotin or a molecule possessing a unique mass or isotope. Alternatively, the set of second agents may include secondary antibodies. After washing away unbound second agents, such as a secondary antibody (e.g., an anti-antibody or a second antibody that binds to another epitope of the antigen associated with the BP biomarker) that is labeled, the presence of one or more of the set of second agents can be used to identify presence of one or more of the set of BP biomarkers. Although embodiments are not so limited, and can include exposing the solid support, which has immobilized antibodies thereon, to the biological sample. Further, other types of tests and assays can be performed, such as PCR-based test and lateral flow assays.

At 214, binding between the set of first agents and the one or more of the set of BP biomarker is identified. The identified binding can depend on the type of assay and/or test performed. For example, some tests, such as lateral flow assays, can result in detected binding that is visible. In other embodiments, the binding is detected using various components to produce and detect electromagnetic radiation, such as a light source producing monochromatic light, prisms, mirrors and lenses to direct and focus the light on the sample detection region, optical filters, apertures and a photodetector to detect light being emitted from the sample detection region, producing a scan of the biological sample detection region that is electronically digitized for communication with signal processing circuitry. The optical scan can be used to identify the locations on the glass slide or other supports or substrates that reveal discrete spots or regions associated with the set of second agents and that correspond to an antibody bound to the one or more of the set of BP biomarkers. As a specific example, if a blood cell exhibits one or more of the set of BP biomarkers, one or more antibodies binds to the one or more BP biomarkers on the glass slide. A set of second agents, such as labeled anti-antibodies, can be applied to the solid support. For example, the anti-antibody, which is fluorescently, enzymatically, or radioactively labeled and washed over the glass slide, binds to the antibody and results in a signal, such as fluorescent emission, when scanned by the optical circuitry.

Other specific embodiments are directed to an apparatus which includes optical components (e.g., fiber optic scanner), a solid support, and processing circuitry. Example optical components include a fiber optic bundle array, a laser, and imaging circuitry (e.g., camera). In specific embodiments, the optical components are used to scan the biological sample, as immobilized and exposed to an antibody to identify antibodies bound to the BP biomarker. The apparatus can include various additional circuitry, such as processing circuitry for controlling the various instruments, memory circuit for storing data sets, and various computer-readable instructions for controlling the optical components and computer-executable instructions (e.g., software) for analyzing data obtained therefrom.

In response to identified binding, at 216, the presence of one or more of the set of BP biomarkers can be detected. Optionally, the subject associated with the biological sample 103 can be ascertained as being infected with BP, and optionally, diagnosed with melioidosis.

In specific embodiments, responsive to the detected presence of BP or relative quantitative amounts of one or more of the set of BP biomarkers, antimicrobial agents can be identified, at 218. The antimicrobial agents can include one or more of Ceftazidime, Meropenem, Trimethoprim-sulfamethoxazole, and/or Doxycycline, among other antimicrobial agents that are known to effective against melioidosis. Based on the identified antimicrobial agents, at 220, a treatment for the subject can be revised, which can include administering the revised treatment, at 222 (e.g., administering a dosage of the antimicrobial agent). The subject can subsequently be re-sampled to re-check for the status of previously identified BP biomarkers.

In various embodiments, exposing the biological sample 103 to the set of first agents can include forming an immuno-assay. For example, a glass substrate or other type of solid support is coated with a biological sample suspected of containing BP biomarkers (e.g., the epitope of the antigen) and used to form an immuno-complex by exposing the immobilized biological sample to the set of first agents (e.g., detection antibodies and optionally, secondary labeled anti-antibodies). The set of first agents can include detection antibodies in such embodiments and are referred as the "detection antibodies" below for ease of reference. An immuno-sandwich can be used to detect antibodies bound to the one or more BP biomarkers. The glass substrate, after washing away unbound detection antibodies, can be treated with a set of second agents that includes labeled secondary antibodies or an anti-antibodies, and an optical scan of the glass substrate is used to identify a signal (e.g., fluorescence) indicative of one or more of the labeled anti-antibodies. If one or more of the set of BP biomarkers is present, a respective detection antibody binds to a complementary BP biomarker present on the glass substrate and the complementary anti-antibody binds to the detection antibody. For example, the anti-antibody can bind to the fragment crystallizable (FC) segment of the detection antibody. Subsequently detected label (associated with the labeled anti-detection antibody) indicates presence of the particular BP biomarker. The anti-antibodies can include various organism-specific antibodies, such as an anti-human antibodies, anti-horse antibodies, anti-dog antibodies, anti-cat antibodies, anti-fish antibodies, anti-cattle antibodies, anti-bird antibodies, among other organisms that have white blood cells and produce antibodies. As may be appreciated, the anti-antibodies used can be specific to the organism, such as an anti-horse detection antibody or an anti-rabbit detection antibody. Similarly, embodiments are not limited to first immobilizing the biological sample and can instead use immobilization of the antibodies or other agents, as further illustrated in FIGS. 3A-3C.

FIGS. 3A-3C illustrate example solid supports for determining a presence of one or more of a set of BP biomarkers or the presence of antibody responses against the one or more BP biomarkers, in accordance with various embodiments. In some embodiments, the exposure of the biological sample to the set of first agents can be used to form an immuno-assay, such as an immuno-sandwich ELISA. In FIGS. 3A-3C, the set of first agents are illustrated and described as being specific to one BP biomarker. However, examples are not so limited and the set of first agents may include agents that specifically bind to more than one of the set of BP biomarkers.

As illustrated by FIGS. 3A and 3B, the biological sample can be immobilized to a solid support 325, which is sometimes referred to herein as a substrate. The immobilized biological sample is exposed to a set of first agents, such as a volume of an antibody. FIG. 3A illustrates an embodiment in which the antibody 327 is labeled such that the antibody 327 is detectable. After incubation of the solid support 325 with a solution containing the antibody 327, the solid support 325 can be washed to remove unbound antibody and is scanned to detect the presence of antibodies 327 bound to the BP biomarker 329 (e.g., a BP biomarker antigen that is associated with a protein secreted by BP). Other embodiments, as illustrated by FIG. 3B, include an assay configuration in which a labeled secondary/anti-antibody 333 that binds to the primary antibody 331 is used to provide the detectable signal and indicate the presence of one or more of the set of BP biomarkers, as illustrated by the particular BP biomarker 329.

In other embodiments, as illustrated by FIG. 3C, the antibody 335 is immobilized to the solid support 325 to capture BP biomarkers 329 when a biological sample is incubated with the solid support 325. The solid support 325 is washed to remove unbound biological sample (which can be further analyzed before or after to determine, e.g., a total cell population in the biological sample and to assess the full population). A set of second agents, which can include a volume of a detection agent, such as a labeled secondary antibody 337, is subsequently applied to the solid support 325. The labeled secondary antibody 337 can be specific to a different epitope of the antigen associated with the BP biomarker 329, although in some cases where the BP biomarker 329 has repetitive epitopes, the labeled secondary antibody 337 can be a labeled version of the immobilized antibody 335. After washing the solid support 325 to remove unbound labeled secondary antibody 337, the solid support 325 is scanned to detect one or more of the labeled secondary antibody 337 bound to the BP biomarker 329 via the antibody 335.

The example solid supports illustrated by FIGS. 3A-3C can additionally and/or alternatively be used to determine the presence of antibody responses against the one or more BP biomarkers. For example, the biological sample can be exposed to the set of BP biomarkers, and the presence of immunoglobulin molecules can be identified based on reactions with the set of BP biomarkers in the biological sample.

Although the embodiments of FIGS. 3A-3C illustrate a flat solid support 325, such as a glass substrate, embodiments are not so limited and can include a variety of different solid supports and assays, such as beads, nanoparticles, tubes, arrays, microfluidic channels, etc. Further embodiments are directed to a set of first agents designed to detect or specifically bind to more than two of the set of BP biomarkers, such as a range of two to ten (or more) BP biomarkers. For example, the embodiments illustrated by FIGS. 3A-3C can include exposing the biological sample to the set of first agents, wherein subsets of the first agents in the set are specific to one or more of a set of BP biomarkers. As a more specific example, a first subset of the set of first agents are specific to a first BP biomarker of the set and a second subset of the set of first agents are specific to a second BP biomarker. The first BP biomarker may be associated with a first protein and the second BP biomarker is associated with a second protein.

FIGS. 4A-4B illustrate example assays for determining a presence of one or more of a set of BP biomarkers, in accordance with various embodiments. More specifically, FIG. 4A illustrates a lateral flow assay and/or test that can be used to test for the presence of BP. As may be appreciated, a lateral flow test, which is also referred to as a lateral flow immunochroatographic assay, is an assay used to test for the presence or absence of a target analyte in a sample and is typically designed as a rapid test that may not require specialized equipment, having a visible readout. An example of such a test is a home pregnancy-test.

As illustrated by FIG. 4A, the assay includes a solid support having a number of different regions 440, 442, 444, 446. The solid support can have at least a first region 440, a second region 442, and a third region 444. At 441, the first region 440 receives a biological sample 451 obtained from a subject. The sample 451 may contain one or more of a set of BP biomarkers, as illustrated by the particular BP biomarker 452. In specific embodiments, at 443, the first region 440 can pass a portion of the sample 451 to the second region 442. For example, the first region 440 can act as a sponge, which in some embodiments can have the desired effect of retaining some interfering molecules while allowing the target analytes unfettered travel along the strip. Once the first region 440 is soaked by the biological sample 451, a portion of the sample 451 migrates to the second region 442 and the remaining portion is held by the first region 440.

The second region 442 includes a set of first agents (e.g., a set of detection agents, such as a set of first antibodies having a label) that are stored within a solid matrix dried onto the support. The set of first agents are specific to the one or more of the set of BP biomarkers, such as the BP biomarker 452, which may include a first epitope of a protein released from BP, although examples are not so limited. For example, the second region 452 can store a conjugate that includes the set of first agents specific to the one or more BP biomarkers dried into a salt-sugar matrix that allows the set of first agents to be stored within the second region 442. As the portion of the biological sample 451 passes into and through the second region 442, the salt-sugar matrix dissolves, releasing the set of first agents into solution where the first agents interact by diffusion with molecules present in the sample 451 and release to further regions of the solid support. The set of first agents can be conjugated to a label (e.g., colored dye), as shown by the particular first agent 453 bound to a label 454 and bound to the BP biomarker 452. The binding of first agents to a BP biomarker forms a detectable complex that can be revealed when reaching the third region 444, as further illustrated at 445. The second region 442 passes at least some portion of the biological sample 451 to the third region 444.

The third region 444 contains a set of second agents (e.g., second antibodies or capture agents) immobilized to the solid support, which can be specific to a second epitope of the protein associated with the one or more BP biomarkers. For example, in response to binding of the first agent 453 (e.g., first antibody) to the BP biomarker 452, a BP biomarker-conjugate complex is formed and is passed to the third region 444. The BP biomarker-conjugate complex binds to the second agent 455 that is formed in a strip or test line in the third region 444. After sufficient fluid has passed the strip, captured BP biomarker-conjugate complexes can accumulate to the level to cause the strip area to become colored. The support may include one or more additional regions 446 that contain immobilized control agents that bind to any particle. The control agents can indicate the functional validity of the assay. For example, as illustrated, the particular first agent 456 containing the label binds to the control agent 457, at 445.

FIG. 4B illustrates a latex agglutination assay that can be used for detecting the presence of one or more BP biomarker sets in a sample. As may be appreciated, a latex agglutination assay, or latex fixation test, is an assay used to test for the presence or absence of BP antigens by coating microbeads 461-1, 461-2, 461-3, 461-P of latex with first agents, 463-1, 463-2, 463-N, such as BP biomarker-specific antibodies. In performing the test, a sample, such as cerebrospinal fluid, serum or urine, is mixed with the coated latex particles in serial dilutions with normal saline to bypass the high-concentration prozone effect and monitored for agglutination (clumping). Agglutination of the beads in any of the dilutions is considered a positive result, confirming that the biological sample contains one or more of the set of BP biomarker sets.

In various embodiments, the microbeads 461-1, 461-2, 461-3, 461-P can be coated with a plurality of different first agents, 463-1, 463-2, 463-N, such as antibodies, as illustrated by 464 and the particular bead 461-1. Each of the different first agents 463-1, 463-2, 463-N can be specific to a respective one (or more) of a set of BP biomarkers 465-1, 465-2, 465-3, 465-4, 465-M. In specific embodiments, a plurality of antibodies are used and at least a portion of the plurality are specific to a different BP biomarker. At 468, the coated beads 461-1, 461-2, 461-3, 461-P are exposed to the biological sample having one or more of a set of BP biomarkers 465-1, 465-2, 465-3, 465-4, 465-M causing agglutination of the beads in response to one or more of the or more of a set of BP biomarkers 465-1, 465-2, 465-3, 465-4, 465-M, for which the first agents 463-1, 463-2, 463-N are designed to specifically bind to, being present in the sample.

A number of more specific embodiments are directed to apparatuses and/or kits used to implement the above described methods. An example kit includes various reagents and a solid support, such as for forming an ELISA assay. The reagents includes a volume of each the set of first agents and a set of labels. Each label of the set can be bound to a respective first agent or the reagents may include a set of second agents bound to the label. The sets of first agents are to bind to one or more of a set of BP biomarkers associated with one or more proteins released from BP or associated with other molecules released from BP as present in the biological sample. The set of labels can bind to the one or more proteins, such as to the first and/or second agents as described above. The solid support can receive application of a biological sample, the set of first agents and the set of labels, and in response, presence of the BP biomarker causes accumulation of one or more of the sets of labels bound to the solid support and indicates the presence of BP in the biological sample within twenty-four hours of the application of the biological sample. The kit may further include a set of second agents and the solid support is to further receive application of the set of second agents. The set of second agents can bind to the set of labels to the one or more proteins, such as by binding directly to a respective protein or by binding to a particular first agent and thereby binding the label to the protein. As may be appreciated, the kit may further include other ancillary materials such as controls and standards to allow medical or laboratory personnel to rapidly and conveniently perform the assay.

An example apparatus includes the various reagents and a solid support having a first region, a second region, and a third region, such as illustrated by FIG. 4A. The first region receives a biological sample or a diluted form of a biological sample obtained from a subject. The second region includes the set of first agents, each bound to a label and adherent on the second region such that interaction of the solid support with the biological sample releases the set of first agents. The set of first agents are specific to one or more of a set of BP biomarkers associated with one or more proteins released from BP cells or associated with other molecules released from BP cells. The third region includes a set of second agents immobilized to the third region and specific to the one or more proteins. In response to application of the biological sample, the first region passes a portion of the biological sample to the second region, and the second region is to pass at least some of the portion of the biological sample to the third region. The presence of the BP biomarker causes accumulation of the label in the third region indicating a presence of BP in the biological sample without culturing the biological sample. In a number of embodiments, the solid support further includes one or more additional regions containing immobilized control agents that bind to the set of first agents.

As may be appreciated, if the BP biomarker is present in the biological sample, one or more of the set of first agents bound to the label (when released from the second region) may bind to the BP biomarker and the BP biomarker then binds to the complementary second agent in the third region. If the BP biomarker is not present in the biological sample, the first agent bound to the label is not bound to anything and, thus there is no BP biomarker to bind to second agent and no label accumulates in the third region.

The above described methods, apparatuses and/or kits can be used for detecting BP biomarker(s) in a biological sample obtained from a subject to infer the existence of an infection caused by BP, to predict the severity of an infection caused by BP, and/or to monitor the course of the disease during treatment of a patient previously diagnosed as having a BP infection. The biological sample may not be cultured, in various embodiments, allowing for detection of BP in less time than a melioidosis infection may kill the subject, such as within twenty-four hours from application of the biological sample.

Experimental/More-Detailed Embodiments

Various embodiments are directed to use of BP biomarkers, such as those associated with a chitin-binding protein (BPSS0493) a protein BPSL1622, a protein BPSL2703, and exported chitinase (BPSL1763). As the BP biomarkers are associated with proteins released from BP cells or other molecules releases from BP cells, the BP biomarkers can be, either directly or in combination with a detection of serological response to BP specific antigens, detected in a culture-independent manner Detection of BP in a subject from a biological sample using one or more of the sets of the BP biomarkers can occur in less than twenty-four hours and/or at a diagnostic sensitivity of greater than sixty percent. As the disease can cause death within twenty-four to forty-eight hours of the onset of symptoms, rapid detection can be beneficial for administering live-saving treatment to the subject in sufficient time to prevent death.

Examples are presented herein describing the detection of one or more of a set of BP biomarkers for both in vitro models of infection and in vivo infections. The in vitro models consist of filtered media from 1) cultured BP strains grown under minimal media conditions, which are meant to approximate the limited nutrient conditions that the bacteria experience in the host and 2) BP co-cultured with human macrophages under conditions where the bacteria interact with and infect the macrophages. The in vivo infections allow serum and/or plasma samples to be generated from 1) experimentally infected non-human primates (NHP) as part of an inhalational-challenge model study and 2) naturally infected patients seeking medical attention upon presentation to a clinic in the melioidosis-endemic area and who were subsequently culture-confirmed as positive for melioidosis. From such studies, candidate BP biomarkers including a chitin-binding protein and the protein BPSL1622 are identified. A number of embodiments that are based on in vitro expression experimental results are recapitulated in animal blood samples for these two example proteins of the candidate BP biomarkers, indicating their utility in aiding in the diagnosis of BP infections. Concentrated culture filtrate from the in vitro culture and infected human macrophage models is characterized in-depth using proteomics, generating an initial biomarker identification including a set of BP biomarkers including the protein BPSL1622, which has low sequence homology to any known protein from any other bacterial species apart from the related pathogen B. mallei. Further experimental embodiments have demonstrated that two members of the set of BP biomarkers, the BP chitin-binding protein, and the protein BPSL1622 were detected in serum samples of the BP-infected NHPs by LC-MS/MS and by ELISA. More recently, the ability to detect has been shown using the example two candidate markers by ELISA in plasma samples collected from acute melioidosis patients as further described in examples herein.

Knowledge of the translated genomic sequences for an initial set of BP biomarkers is used to manufacture synthetic genes that are cloned into plasmids to express affinity-tagged recombinant proteins. The recombinant proteins allow for the generation of monoclonal antibodies and the development and performance characterization of the antibody responses for ELISA. Experimental embodiments illustrate the utility of using these for affinity purification of anti-target antibodies as tools for enriching and detecting additional novel antigens.

In Vitro Bacterial Culture Study to Generate Samples for Biomarker Identification To preserve the proteins as closely as possible to their native states, culture broth are filter sterilized for a safe removal of samples out of a BSL-3 containment. Cultures are made in triplicate using modified minimal defined-medium (M9) for the two BP strains, K96243 and HBPUB10303a, which have been genotyped previously for quality control.

LC-MS/MS Proteomics Analysis for Biomarker Identification in Culture Filtrates

Protein expressions of potential biomarkers are evaluated using a high-resolution mass spectrometry (MS) instrument. To establish that the culture medium employed does not interfere with downstream processing and LC-MS/MS analysis, a key set of method development samples is processed and an LC-MS/MS proteome analysis is performed on them to confirm that the bacteria used are in BP and the tested culture conditions are able to release sufficient amount of proteins into the culture medium. In a specific experimental embodiment, an example for the comparison of the relative amount or spectra counts of each identified protein in each sample from the two BP strains grown to stationary phase in modified M9 medium is shown in Table 1, which is also Table 1 of the underlying Provisional Application.

The example data of Table 1 shows the expression of the forty identified proteins in the culture filtrate of the M9 medium. The number of spectral counts, unique spectra counts and percent sequence coverage that are observed in specific experimental embodiments for the triplicate cultures of each strain are presented in Table 1 and is ranked by a sum of all spectral counts as an approximation of relative protein abundance in the culture medium. Many proteins that have similar levels across the triplicates, demonstrating consistency of the cultures.

The example results show that a set of proteins is enriched in the culture filtrates relative to the majority proteins in whole cell lysates. These proteins include not only a family of bacterial proteins known to be secreted by many species, such as flagellin and peptidase, and a group of proteins that have not been reported before. Two such proteins are chitin-binding protein and protein BPSL2703 from BP. The sequence of this protein has relatively low homology to other species except *Burkholderia mallei* (BM) and *Burkholderia thailandensis* (BT), making it an attractive antigen candidate. This finding can be used to develop a targeted assay using chitin beads, as described in a specific experimental embodiment.

TABLE 1

Top-40 proteins identified in culture filtrate samples from triplicate cultures of the two exemplary BP strains, K96243 and HBPUB10303a grown in M9 medium.

| | | | Qualified K96243 | | | | | | Qualified HBPUB-101303a | |
|---|---|---|---|---|---|---|---|---|---|---|
| Rank | # AAs | Protein | # Spectra | # Uniq | Coverage | # Spectra | # Uniq | Coverage | # Spectra | # Uniq |
| 1 | 171 | BPSL2703 | 628 | 91 | 80.1 | 724 | 93 | 80 | 610 | 92 |
| 2 | 365 | chitin-binding protein | 227 | 67 | 72.9 | 232 | 75 | 76 | 209 | 64 |
| 3 | 457 | exported chitinase | 92 | 39 | 66.1 | 97 | 42 | 64 | 78 | 35 |
| 4 | 388 | flagellin | 72 | 37 | 61.9 | 86 | 52 | 68 | 88 | 49 |
| 5 | 500 | serine metalloprotease precursor | 26 | 19 | 30.4 | 40 | 26 | 37 | 19 | 13 |
| 6 | 567 | thermolysin metallopeptidase | 32 | 19 | 43.7 | 38 | 22 | 46 | 33 | 20 |
| 7 | 301 | outer membrane protein | 12 | 7 | 34.9 | 16 | 10 | 35 | 13 | 9 |
| 8 | 466 | BPSS1588 | 15 | 12 | 32.2 | 21 | 18 | 42 | 19 | 16 |
| 9 | 182 | hydroperoxide reductase | 23 | 13 | 74.7 | 24 | 14 | 79 | 25 | 15 |
| 10 | 546 | molecular chaperone GroEL | 29 | 20 | 43.8 | 24 | 17 | 44 | 28 | 19 |
| 11 | 408 | aminopeptidase | 23 | 13 | 42.2 | 26 | 14 | 45 | 19 | 10 |
| 12 | 645 | peptidase | 15 | 10 | 20.6 | 20 | 15 | 26 | 16 | 11 |
| 13 | 284 | IclR family transcriptional regulator | 13 | 1 | 2.8 | 10 | 2 | 9 | 11 | 1 |
| 14 | 90 | BPSL2251 | 4 | 3 | 27.8 | 3 | 3 | 28 | 3 | 3 |
| 15 | 164 | BPSS0985 | 3 | 3 | 29.3 | 7 | 3 | 29 | 6 | 5 |
| 16 | 615 | lipoprotein | 0 | | | 1 | 1 | 2 | | |
| 17 | 132 | outer membrane protein | 5 | 4 | 25.8 | 7 | 4 | 26 | 7 | 4 |
| 18 | 555 | oxygenase | 6 | 3 | 2.5 | | | | 4 | 3 |
| 19 | 1111 | BPSL2046 | 6 | 2 | 3.4 | 2 | 1 | 1.0 | 5 | 1 |
| 20 | 411 | BPSS0580 | 0 | | | 5 | 3 | 13 | | |
| 21 | 342 | phosphate transport system | 6 | 5 | 32.8 | 3 | 3 | 18 | | |
| 22 | 410 | fatty acid desaturase | 4 | 4 | 11.5 | 3 | 3 | 12 | | |
| 23 | 667 | flagellar hook-associated protein FlgK | 4 | 4 | 11.7 | 2 | 2 | 6 | 7 | 6 |
| 24 | 249 | electron transfer flavoprotein subunit | 3 | 1 | 3.2 | 5 | 1 | 3 | 2 | 1 |
| 25 | 614 | peptidoglycan synthetase FtsI | 6 | 4 | 15.2 | | | | | |

TABLE 1-continued Top-40 proteins identified in culture filtrate samples from triplicate cultures of the two exemplary BP strains, K96243 and HBPUB10303a grown in M9 medium.

| | | | | | | | | | | |
|---|---|---|---|---|---|---|---|---|---|---|
| 26 | 721 | peptidase | 0 | | | 1 | 1 | 2 | 3 | 3 |
| 27 | 300 | glutamate/aspartate periplasmic binding | 1 | 1 | 4.0 | 1 | 1 | 4 | 2 | 2 |
| 28 | 108 | thioredoxin 1 | 1 | 1 | 10.2 | 2 | 2 | 19 | 2 | 2 |
| 29 | 151 | BPSL1067 | 1 | 1 | 12.6 | 2 | 2 | 21 | 3 | 2 |
| 30 | 107 | BPSS0767 | 2 | 2 | 18.7 | 1 | 1 | 9 | 1 | 1 |
| 31 | 212 | thiol:disulfide interchange protein | 1 | 1 | 9.9 | 2 | 2 | 10 | 4 | 4 |
| 32 | 327 | malate dehydrogenase | 5 | 3 | 14.7 | 2 | 2 | 20 | 1 | 1 |
| 33 | 79 | acyl carrier protein | 3 | 2 | 32.9 | 2 | 2 | 33 | 2 | 2 |
| 34 | 4574 | polyketide synthase | 0 | | | | | | | |
| 35 | 251 | BPSL1193 | 3 | 3 | 18.3 | | | | 4 | 3 |
| 36 | 1191 | 2-oxoacid ferredoxin oxidoreductase | 1 | 1 | 1.0 | 2 | 2 | 2 | | |
| 37 | 641 | selenocysteine-specific elongation | 0 | | | 2 | 2 | 3 | 2 | 2 |
| 38 | 650 | molecular chaperone DnaK | 3 | 3 | 5.4 | 1 | 1 | 2 | 2 | 2 |
| 39 | 256 | BPSL1622 | 2 | 2 | 9.0 | 2 | 2 | 9 | 1 | 1 |
| 40 | 158 | BPSS1849 | 1 | 1 | 30.4 | 2 | 2 | 30 | 2 | 2 |

| | Qualified HBPUB-101303a | | | | | | | | | | Sum of # |
|---|---|---|---|---|---|---|---|---|---|---|---|
| Rank | Coverage | # Spectra | # Uniq | Coverage | # Spectra | # Uniq | Coverage | # Spectra | # Uniq | Coverage | Spectra |
| 1 | 80.1 | 595 | 94 | 80.1 | 808 | 102 | 80.1 | 730 | 88 | 80.1 | 4095 |
| 2 | 78.4 | 233 | 75 | 73.7 | 385 | 94 | 75.6 | 268 | 78 | 82.2 | 1554 |
| 3 | 61.1 | 105 | 47 | 66.1 | 163 | 50 | 68.1 | 120 | 43 | 66.5 | 655 |
| 4 | 67.5 | 48 | 32 | 58.8 | 96 | 54 | 67.5 | 51 | 34 | 65.0 | 441 |
| 5 | 24.8 | 42 | 22 | 32.4 | 53 | 28 | 38.0 | 39 | 21 | 30.2 | 219 |
| 6 | 41.8 | 21 | 17 | 38.6 | 34 | 19 | 41.3 | 22 | 16 | 35.5 | 180 |
| 7 | 37.2 | 24 | 14 | 41.2 | 38 | 19 | 44.2 | 28 | 11 | 35.2 | 131 |
| 8 | 42.1 | 24 | 19 | 42.3 | 31 | 20 | 47.4 | 17 | 15 | 42.7 | 127 |
| 9 | 80.2 | 12 | 8 | 56.0 | 18 | 12 | 81.3 | 16 | 11 | 77.5 | 118 |
| 10 | 48.4 | 5 | 4 | 12.5 | 16 | 12 | 29.1 | 14 | 9 | 23.3 | 116 |
| 11 | 35.1 | 13 | 10 | 32.6 | 18 | 14 | 42.7 | 12 | 7 | 30.6 | 111 |
| 12 | 19.1 | 14 | 10 | 16.6 | 22 | 15 | 25.7 | 11 | 9 | 19.1 | 98 |
| 13 | 2.8 | 13 | 2 | 8.5 | 12 | 1 | 2.8 | 11 | 1 | 2.8 | 70 |
| 14 | 27.8 | 6 | 4 | 47.8 | 12 | 5 | 47.8 | 6 | 4 | 47.8 | 34 |
| 15 | 29.3 | 6 | 3 | 29.3 | 5 | 4 | 29.3 | 7 | 5 | 55.5 | 34 |
| 16 | | 7 | 7 | 14.5 | 10 | 7 | 20.2 | 7 | 7 | 19.7 | 25 |
| 17 | 25.8 | 1 | 1 | 6.8 | 1 | 1 | 6.8 | 1 | 1 | 6.8 | 22 |
| 18 | 2.5 | | | | 6 | 3 | 2.5 | 3 | 3 | 6.1 | 19 |
| 19 | 1.0 | 2 | 2 | 4.4 | 3 | 2 | 3.3 | 1 | 1 | 1.0 | 19 |
| 20 | | 3 | 2 | 8.0 | 6 | 3 | 8.0 | 3 | 3 | 8.0 | 17 |
| 21 | | | | | 5 | 5 | 15.2 | | | | 14 |
| 22 | | 6 | 5 | 23.4 | | | | | | | 13 |
| 23 | 16.2 | | | | | | | | | | 13 |
| 24 | 3.2 | | | | 2 | 1 | 3.2 | 1 | 1 | 3.2 | 13 |
| 25 | | 1 | 1 | 1.3 | 5 | 4 | 7.7 | | | | 12 |
| 26 | 5.3 | 2 | 2 | 4.0 | 3 | 3 | 10.8 | 3 | 3 | 5.4 | 12 |
| 27 | 8.3 | | | | 4 | 3 | 17.0 | 3 | 3 | 15.3 | 11 |
| 28 | 18.5 | 2 | 2 | 18.5 | 2 | 2 | 18.5 | 2 | 2 | 18.5 | 11 |
| 29 | 21.2 | 2 | 2 | 21.2 | 2 | 2 | 21.2 | 1 | 1 | 12.6 | 11 |
| 30 | 9.4 | 2 | 2 | 18.7 | 3 | 2 | 18.7 | 1 | 1 | 9.4 | 10 |
| 31 | 29.3 | 1 | 1 | 7.1 | 1 | 1 | 9.9 | 1 | 1 | 9.9 | 10 |
| 32 | 3.7 | | | | | | | | | | 8 |
| 33 | 32.9 | 1 | 1 | 15.2 | | | | | | | 8 |
| 34 | | 8 | 7 | 4.3 | | | | | | | 8 |
| 35 | 18.7 | | | | | | | | | | 7 |
| 36 | | 4 | 4 | 6.2 | | | | | | | 7 |
| 37 | 6.2 | 1 | 1 | 1.3 | 1 | 1 | 1.3 | 1 | 1 | 1.3 | 7 |
| 38 | 3.2 | | | | | | | | | | 6 |
| 39 | 4.7 | 1 | 1 | 4.7 | | | | | | | 6 |
| 40 | 30.4 | 1 | 1 | 30.4 | | | | | | | 6 |

In Vitro Macrophage Infection Co-Culture Study to Generate Samples for Identification of Additional Biomarkers that can be Induced and Released when the BP Encountering Mammalian Host Cells In accordance with various experimental embodiments, an improved list of BP-specific biomarkers is generated by corroborating reported candidate BP biomarkers and identifying new ones. For this purpose, a robust macrophage infection model can be established and preliminary LC-MS/MS biomarker analysis is performed on those samples for the markers that may be produced from in vitro intracellular infections.

To establish the infection model, various experimental embodiments involve the use of two human monocyte cell lines, THP-1 and U937 and a human lung epithelial cell line, A549.

The differentiation of monocytes into macrophages are optimized for conducting infection tests, and co-culture conditions are developed for the evaluation of biomarkers that may be produced from intra-cellular infections.

Three (initial) experiments are performed to obtain optimized conditions for the final large-scale definitive experiment with the conditions summarized below, and which are further illustrated in Table 2 below, which includes Table 2 of the underlying Provisional Application. The conditions include human cells THP-1, a culture medium during infection of RPMI Serum free Phenol red free, a target multiplicity of infection (MOI) of 20:1, a total incubation time of around 13 hours, and time between infection and PMA removal of 16 hours. The experiments were performed using a qualified strain of K96243.

for two days at 37° C. in the presence of five percent $CO_2$ and then switched to PMA-free RPMI medium sixteen hours prior to the BP uptake. BP infection is performed in phenol red free, serum-free RPMI medium to maximize the identification of protein biomarkers by LC-MS/MS.

After around thirteen hours total incubation with BP bacteria, a large number of human cells are found to be infected with BP. Concentrated medium supernatants are prepared for in-depth biomarker analysis (30× sample 1 from BP infected co-cultures and 12× sample 2 from THP-1 cell alone). Sterility of samples can be verified on both agar plates and in liquid cultures prior to the release for LC-MS/MS analysis, as further described herein.

LC-MS/MS Proteomics Analysis of Co-Culture Samples for Biomarker Identification LC-MS/MS analysis of co-culture supernatants generated from the large-scale definitive study can be performed for obtaining information about the updated list of biomarker candidates.

Analysis of the results focused on BP proteins can show more proteins and/or peptides identified in the scaled-up concentrated culture medium compared with the initial experiments done with bacterial culture. As demonstrated by Table 3, which includes Table 3 of the underlying Provisional Application, for example, the protein BPS1622 is identified with seventeen unique peptides corresponding to a protein coverage of 78.5 percent in the large scale co-culture study (labeled as K96243) strain, whereas in the

TABLE 2

Co-culture study summary

| Experiment | Culture Conditions: Human Cells | Culture medium during infection | Target MOI** | Total incubation time | Time between infection and PMA removal |
|---|---|---|---|---|---|
| Large-scale* | THP-1 | RPMI Serum free Phenol red free | 20:1 | ~13 hours | 16 hours |

*Experiments were performed using qualified strain K96243,
**Multiplicity Of Infection (MOI)

The experimental embodiment study (large-scale) can provide sufficient materials for in-depth marker analysis by LC-MS/MS. In brief, a total of thirty-one 6-well plates of human macrophages, differentiated from THP-1 cells are used in the study. In specific embodiments, these include twenty plates for the infection with BP from the BP strain, K96243, ten plates for THP-1 cells alone as controls, and one plate for initial THP cell count.

THP-1 monocyte cells are plated and differentiated in PMA (Phorbol-12-myristate-13-acetate) into macrophages initial bacterial culture filtrate study, no peptide is found for this protein. Identifications in the additional experimental embodiments can also include many protein entries that are seen in the initial bacterial culture study, for example BP chitin-binding protein, protein BPS2703, flagellin and flagellin hook-associated protein, etc. The scaled-up experimental embodiment provides not only a confirmation for the initial experiment, but also proteins that might be induced and released when the BP is growing within the mammalian host cells.

TABLE 3

Top-20 BP Proteins identified in co-culture medium of a scaled-up experiement with the K96243 strain.

| Filtered for BP Proteins: Rank | # AAs | Description | K96243: # Spectra | # Uniq | Coverage |
|---|---|---|---|---|---|
| 1 | 256 | BPSL1622 | 26 | 17 | 78.5 |
| 2 | 171 | BPSL2703 | 12 | 9 | 76.6 |

TABLE 3-continued Top-20 BP Proteins identified in co-culture medium
of a scaled-up experiement with the K96243 strain.

| | Filtered for BP Proteins | | K96243 | | |
|---|---|---|---|---|---|
| Rank | # AAs | Description | # Spectra | # Uniq | Coverage |
| 3 | 388 | flagellin | 9 | 7 | 40.0 |
| 4 | 645 | peptidase | 9 | 9 | 19.1 |
| 5 | 396 | elongation factor Tu | 8 | 7 | 23.7 |
| 6 | 507 | flagellar hook-associated protein | 5 | 4 | 11.4 |
| 7 | 567 | thermolysin metallopeptidase | 4 | 4 | 11.3 |
| 8 | 546 | molecular chaperone GroEL | 3 | 2 | 6.6 |
| 9 | 365 | chitin-binding protein | 3 | 3 | 9.6 |
| 10 | 466 | BPSS1588 | 3 | 3 | 7.7 |
| 11 | 667 | flagellar hook-associated protein FlgK | 2 | 2 | 5.9 |
| 12 | 457 | exported chitinase | 2 | 2 | 9.4 |
| 13 | 97 | co-chaperonin GroES | 2 | 2 | 27.8 |
| 14 | 132 | outer membrane protein | 2 | 2 | 18.9 |
| 15 | 114 | negative regulator of flagellin synthesis | 1 | 1 | 16.7 |
| 16 | 410 | flagellar hook-associated protein FlgL | 1 | 1 | 7.6 |
| 17 | 249 | phosphoglyceromutase | 1 | 1 | 4.0 |
| 18 | 293 | elongation factor Ts | 1 | 1 | 8.5 |
| 19 | 684 | amino acid dioxygenase | 1 | 1 | 1.3 |
| 20 | 348 | BPSS0841 | 1 | 1 | 2.0 |

List of the New Candidate Protein Markers

The attached sequence listing includes sequences of the identified proteins as listed in Table 4 (also referred to as Table 4 in the underlying Provisional Application) an example of twelve of the candidate protein markers, e.g., the BP biomarkers that are identified using the in vitro culture and co-culture models. These proteins are selected using a combination of sequence coverages for the proteins identified from the analysis of the culture supernatant and co-culture supernatants respectively using spectra counts. The proteins include BPSS0493, BPSL1622, BPSL2703, BPSL1763, BPSL3319, BPSS0827, BPSL3215, Little is known about the bacterial protein BPSL1622 which expression is up-regulated during interaction with host cells. This protein is an attractive candidate because it appears to be unique to BP and some strains of the other related pathogenic Burkholdria species, *B. mallei*. No other bacterial species appears to have greater than 50% sequence identity to BPSL1622 when submitted to a BLAST search against protein databases available to date and it does not contain any known homologous conserved domains.

TABLE 4

List of the Candidate Protein Markers

| Bacterial Protein Name(Locus Tag) | Protein Sequence (in sequence listing) |
|---|---|
| Chitin-binding protein (BPSS0493) | SEQ. 1: YP_110514.1 chitin-binding protein [BP K96243] |
| Protein (BPSL1622) | SEQ. 2: YP_108236.1 protein BPSL1622 [BP K96243] |
| Protein (BPSL2703) | SEQ. 3: YP_109299.1 protein BPSL2703 [BP K96243] |
| Exported chitinase (BPSL1763) | SEQ. 4: YP_108363.1 exported chitinase [BP K96243] |
| Flagellin (BPSL3319) | SEQ. 5: YP_109915.1 flagellin [BP K96243] |
| Peptidase (BPSS0827) | SEQ. 6: YP_110838.1 peptidase [BP K96243] |
| Elongation factor Tu (BPSL3215) | SEQ. 7: YP_109809.1 elongation factor Tu [BP K96243] |
| Flagellar hook-associated protein (BPSS0860) | SEQ. 8: YP_110870.1 flagellar hook-associated protein [BP K96243] |
| Thermolysin metallopeptidase (BPSS0564) | SEQ. 9: YP_110585.1 thermolysin metallopeptidase [BP K96243] |
| Molecular chaperone GroEL (BPSL2697) | SEQ. 10: YP_109293.1 molecular chaperone GroEL [BP K96243] |
| Protein (BPSS1588) | SEQ. 11: YP_111596.1 hypothetical protein BPSS1588 [BP K96243] |
| Outer membrane protein (BPSL3331) | SEQ. 12: YP_109927.1 outer membrane protein [BP K96243] |

Bioinformatics (Sequence Alignment)

BP genome is known to be unstable. Proteins that have relatively stable protein sequences were analyzed for sequence alignments to ensure low degree of protein sequence variability across all strains using publicly available databases with ~730 sequenced BP and *B. thailandensis* (BT) strains and sub-strains.

For marker candidate BPSL1622, because it is not well characterized at the protein level and the automated gene translation on the NCBI portal was determined to have inconsistencies, the degree of genomic variability across ~730 sequenced strains was looked at. There is a low degree of variability with only 0-9 nucleotide differences; however, because of codon redundancy, nucleotide changes do not necessarily mean changes in protein sequence. There are examples of silent polymorphism in the BPSL1622 gene sequence (e.g., AAG and AAA are both codons for lysine), coding repeats for amino acids (PLM—which probably do not have a functional impact and could be probed later for epitope significance), variations in signal sequence with no amino acid changes in secreted protein, and single changes in codon (AGC for Ser changed to AAC codon for Asn). A BLAST of BPSL1622 against *B. thailandensis* genomes was also performed and found only weak alignments; scattered and short segments were found between BP and BT strains. The gene for BPSL1622 does not occur in BT or may be greatly mutated as there is nothing found with any significant degree of homology.

NHP Study

An animal study of melioidosis in NHPs with a time course of infection and physiological response similar to humans was conducted in Battelle to generate serum samples. Specific experimental embodiments are directed to observing infection for inhalation-acquired melioidosis in the rhesus macaque. For example, the subjects are adult rhesus macaques (*Macaca mulatta*) that are aerosol challenged with two BP strains (K96243 and HBPUB10303a) via head-only inhalation infection route. The subjects have a target inhaled dose of 1000 cfu/animal. In specific embodiments, the measured inhaled dose is 600-3000 cfu/animal. K96243 infected macaques can be expected die between three to twelve days after infection, with many deaths occurring in the first seven days post-exposure and with a few surviving. Serum from the subjects were analyzed for biomarkers.

Human Clinical Samples

A high-quality reference set of patient samples are assembled for biomarker identification. In specific experimental embodiments, the collection and preparation of human patient samples were conducted in Cambodia under the guidance of the Institute of Tropical Medicine (ITM).

To proceed with the collection and analysis of human plasma and serum samples from infected patients, clinical samples were obtained from a melioidosis clinical study at Sihanouk Hospital Center of Hope (SHCH), in Penh, Cambodia, and HOPE Community Medical Center (CMC). The study protocols are approved by the National Ethics Committee for Health Research in Cambodia, the Institutional Review Board (IRB) at ITM, and also the Ethics Committee in University of Antwerp.

Sterilization of NHP and Patient Samples in BSL-3 Laboratory

Patient and NHP samples are processed following a validated filter-sterilization procedures. Aliquots of samples are released after confirmation of sterilization of samples using 10% of the materials for each one.

Biomarker Characterization Using the NHP Study Samples

New Enrichment Method Using Chitin Affinity Beads to Confirm and Characterize BP-Specific Chitin-Binding Protein To follow-up on analyzing potential new BP-specific protein biomarker candidates, new enrichment methods for targeting BP-specific chitin-binding protein can be developed.

If the abundant chitin-binding protein that is identified in the BP culture supernatant is functional and capable of binding to chitin, then chitin beads may be used as an affinity enrichment method to allow for capturing and detection of the protein in clinical and NHP samples. To test for this, BP culture filtrate samples spiked into human plasma samples at ten percent and one percent (v:v) levels are prepared and used to test the ability of chitin magnetic beads to capture and enrich the chitin-binding protein from plasma. In specific experimental embodiments, for an initial test, fifty microliters of chitin magnetic beads (New England Biolabs, Lot #0041508) are used. The beads are prepared according to the manufacturer's protocol and plasma samples ranging from 100-500 microliters, with and without spiked BP culture supernatant, are incubated with the beads for one hour at room temperature. Unbound plasma is removed on a magnetic separator, and the beads are washed three times. In order to test for captured chitin-binding protein, the beads are suspended in fifty mM ammonium bicarbonate buffer (pH 8.3) and two micrograms of trypsin is added directly to the suspended beads. The beads are incubated with trypsin for fourteen hours, at which time the supernatant is removed, acidified and analyzed by LC-MS/MS.

In various experimental embodiments, an optimized LC-MS/MS assay enables the detection of the BP chitin-binding protein at the low ng/ml level.

FIG. 5 is a schematic of an example protocol for in vivo detection of the chitin-binding protein by LC-MS/MS, in accordance with various embodiments. More specifically, FIG. 5 illustrates an example of what has been detected in an LC-MS/MS method of the chitin-binding protein from a blood sample, at 570, of an animal infected in vivo with BP, at 572 and 573, in accordance with various embodiments.

FIG. 6 illustrates representative LC-MS/MS data for detecting a tryptic peptide derived from the chitin-binding protein captured from a BP-infected NHP serum sample collected at the terminal bleed, in accordance with various embodiments. The illustration includes an example of LC-MS/MS data for two different tryptic peptides derived from the chitin-binding protein captured from human plasma at the one percent spiked level and from BP-infected NHPs at the terminal bleed, in accordance with various embodiments. In specific experimental embodiments, no signal is detected for these peptides in negative controls (pre-infection NHP serum and un-spiked human plasma). These results illustrate that this can be used as a method to enrich this marker protein from clinical samples and NHP-study samples.

More specifically, FIG. 6 illustrates representative LC-MS/MS data for detecting a tryptic peptide (AFVEPGIAPR) derived from the chitin-binding protein captured from a BP-infected NHP serum sample collected at the terminal bleed (Day 4 post challenge). The sample is enriched from a human plasma sample that is spiked at the one percent level with BP culture supernatant. The sequence of this peptide, AFVEPGIAPR, is unique to BP, and which is identified by SEQ. ID 13.

ELISA Assays Developed to Characterize BP Chitin-Binding Protein and BPSL1622

To confirm these identified candidates shown in Table 4, E. coli expression plasmids can be ordered from DNA 2.0 for the new targets. Recombinant proteins can be expressed and purified to generate customized polyclonal and monoclonal antibodies for the development of customized ELISA assays. In a number of experimental embodiments, ELISA assays developed are used to confirm and characterize time profiles of the new markers during the course of infection using the NHP inhalation model as previously described.

FIG. 7 is a schematic of an example ELISA assay for characterizing the BP chitin-binding protein and identifying candidate panels for clinical diagnosis of melioidosis, in accordance with various embodiments. The time profiles of the BP chitin-binding protein marker are evaluated by the developed ELISA assay in serum samples collected from infected NHPs. In the particular example, a capture antibody 773 (e.g., monoclonal anti-CBP capture antibody/clone 4B2) is immobilized on the solid support 770. The capture antibody 773 binds to the target protein 775 (e.g., BP chitin-binding protein) present in the sample. A detection antibody 777 (e.g., polyclonal anti-CBP detection antibody) binds to another region of the target protein 775, and an anti-antibody 779 (e.g., HRP-conjugated secondary reporter) binds to the detection antibody 777, and the label 778 binds thereto.

FIGS. 8A-8D illustrate example ELISA results for the detection of BP chitin-binding protein biomarkers in (four) BP-infected NHPs, in accordance with various embodiments. As illustrated by FIGS. 8A-8D, the chitin-binding protein are detected in day 3 and 4 post-challenge samples with the current assay limit of detection of 50-100 µg/mL in neat samples. This shows a potential use of the protein as a pathogen diagnosis test marker for BP infection.

FIG. 9 is a schematic of an example ELISA assay for characterizing BPSL1622 and identifying candidate panels for clinical diagnosis of melioidosis, in accordance with various embodiments. The time profile of the BPSL1622 marker are also evaluated by another developed ELISA assay with chemiluminescent detection as illustrated by FIG. 9. In the particular example, a capture antibody 983 (e.g., polyclonal anti-1622 anti-CBP capture antibody) is immobilized on the solid support 980. The capture antibody 983 binds to the target protein 985 (e.g., BPSL1622 protein) present in the sample. A detection antibody 987 (e.g., monoclonal anti-1622 detection antibody) binds to another region of the target protein 885 (e.g., BPSL1622), and an anti-antibody 989 (e.g., HRP-conjugated secondary reporter) binds to the detection antibody 987 which binds to the label 986.

FIGS. 10A-10D illustrate example results for the detection of the BPSL1622 by ELISA in (four) BP-infected NHPs, in accordance with various embodiments. As illustrated by FIGS. 10A-10D, BPSL1622 are detected in day 3 and 4 post-challenge samples with the current assay limit of detection of 350-600 µg/mL. This also shows a potential use of this protein as a unique pathogen diagnosis test marker for BP infection.

Serological IgG Host-Response ELISA Assays Also Developed to Characterize New Markers FIG. 11 is a schematic of an ELISA method for detecting IgG host-response to the BP antigens in accordance with various embodiments. Time-course data for NHP IgG host-responses against the BP recombinant proteins in BP infected NHPs can also be studied by an indirect ELISA assay as illustrated by FIG. 11. As shown, the biological sample is immobilize to the solid support, as illustrated by the particular BP biomarker 1103. A primary antibody 1105 binds to the BP biomarker 1103, and a secondary antibody 1107 binds to the primary antibody 1107 and is exposed to the label 1109.

As illustrated above, chitin-binding protein, exported chitinase and BPSL2703 show clear IgG response in an infected NHP model, demonstrating a potential use of these candidate markers as a serological diagnosis test for BP infection.

Figure 3A:
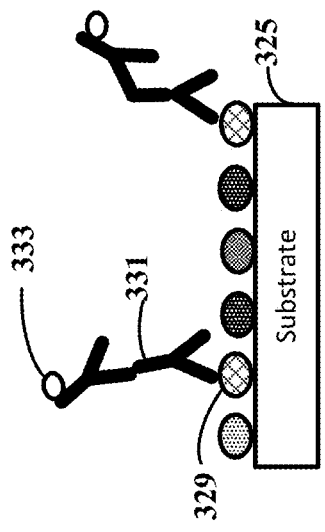
Figure 3B:
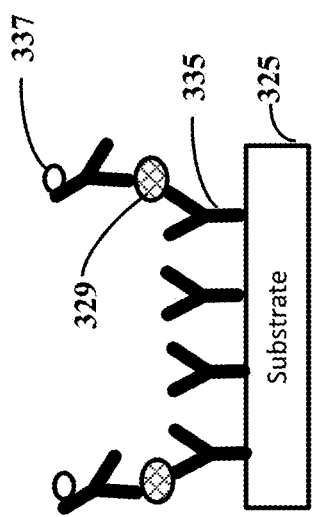
Figure 3C:
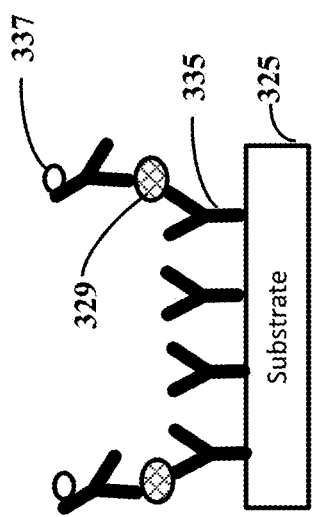
Figure 4A:
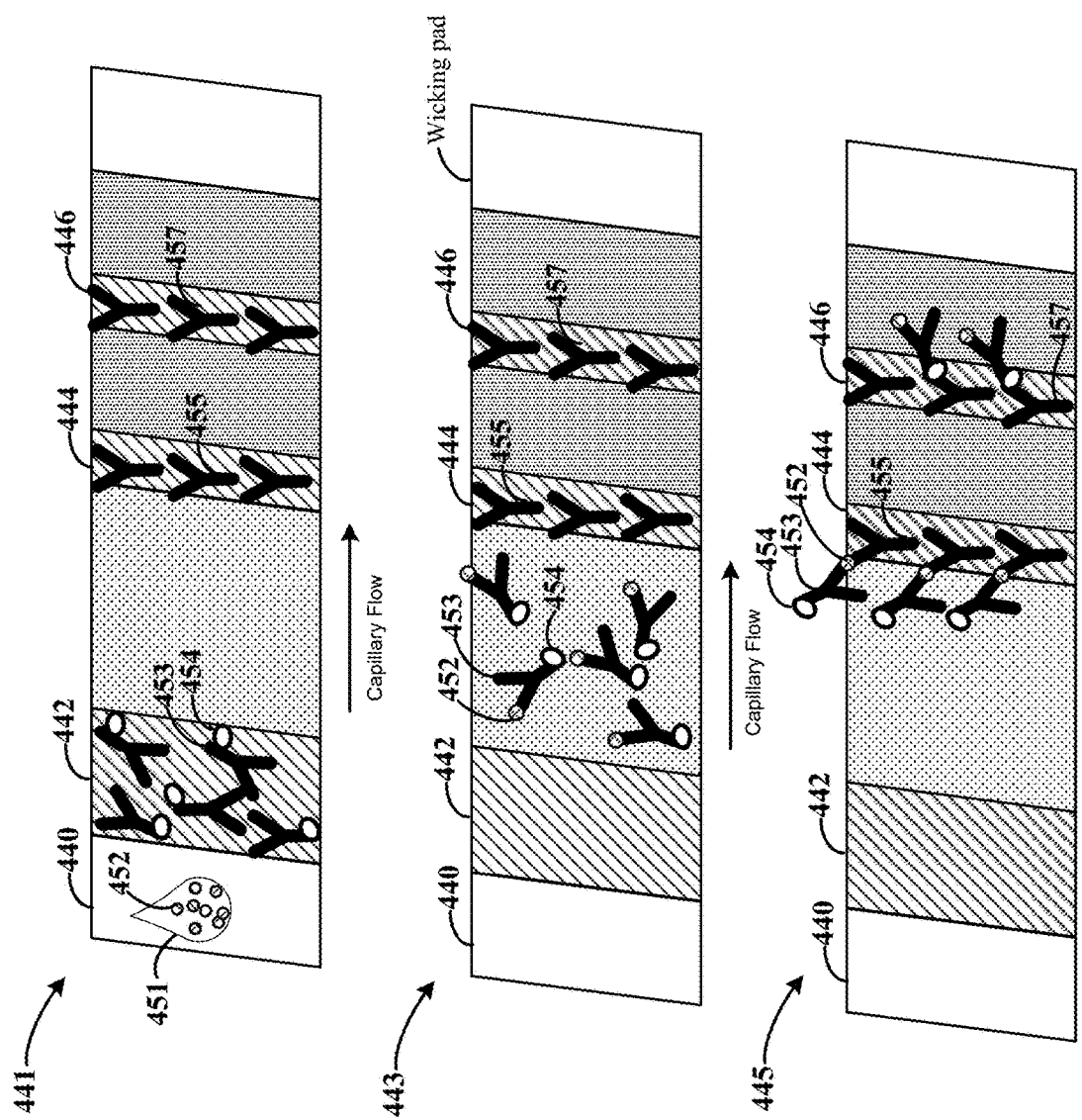
Figure 4B:
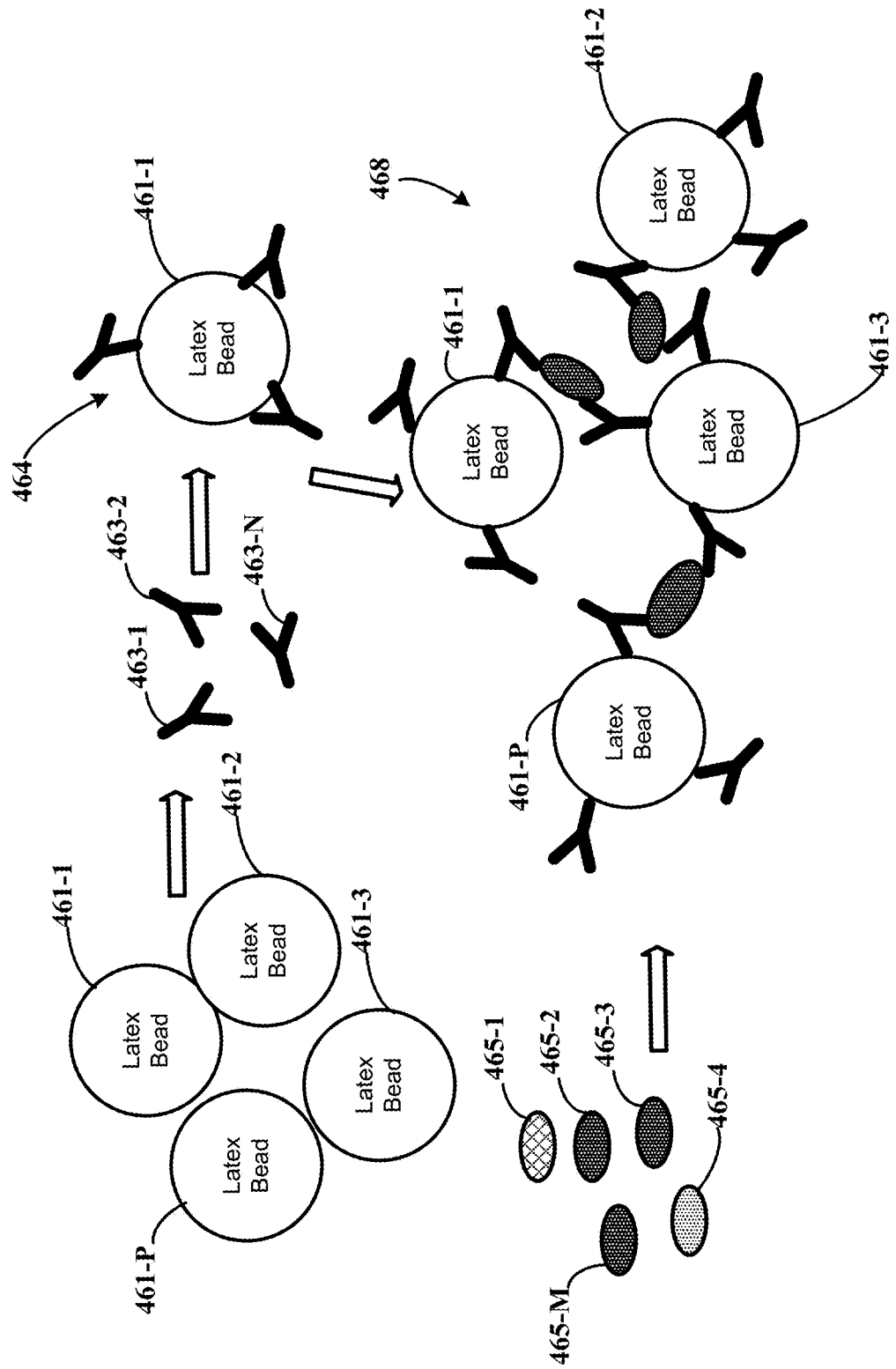
Figure 5:
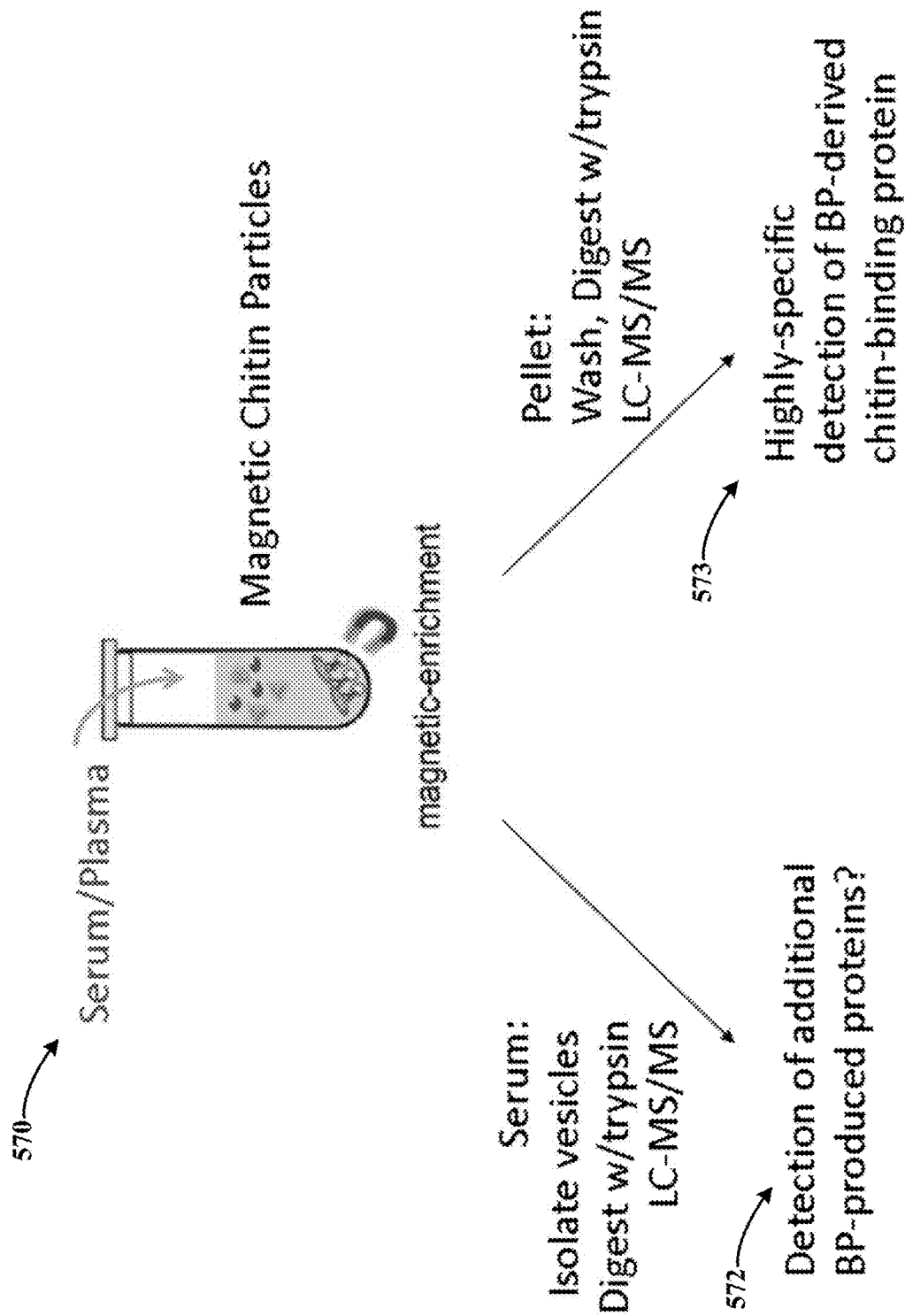
Figure 6:
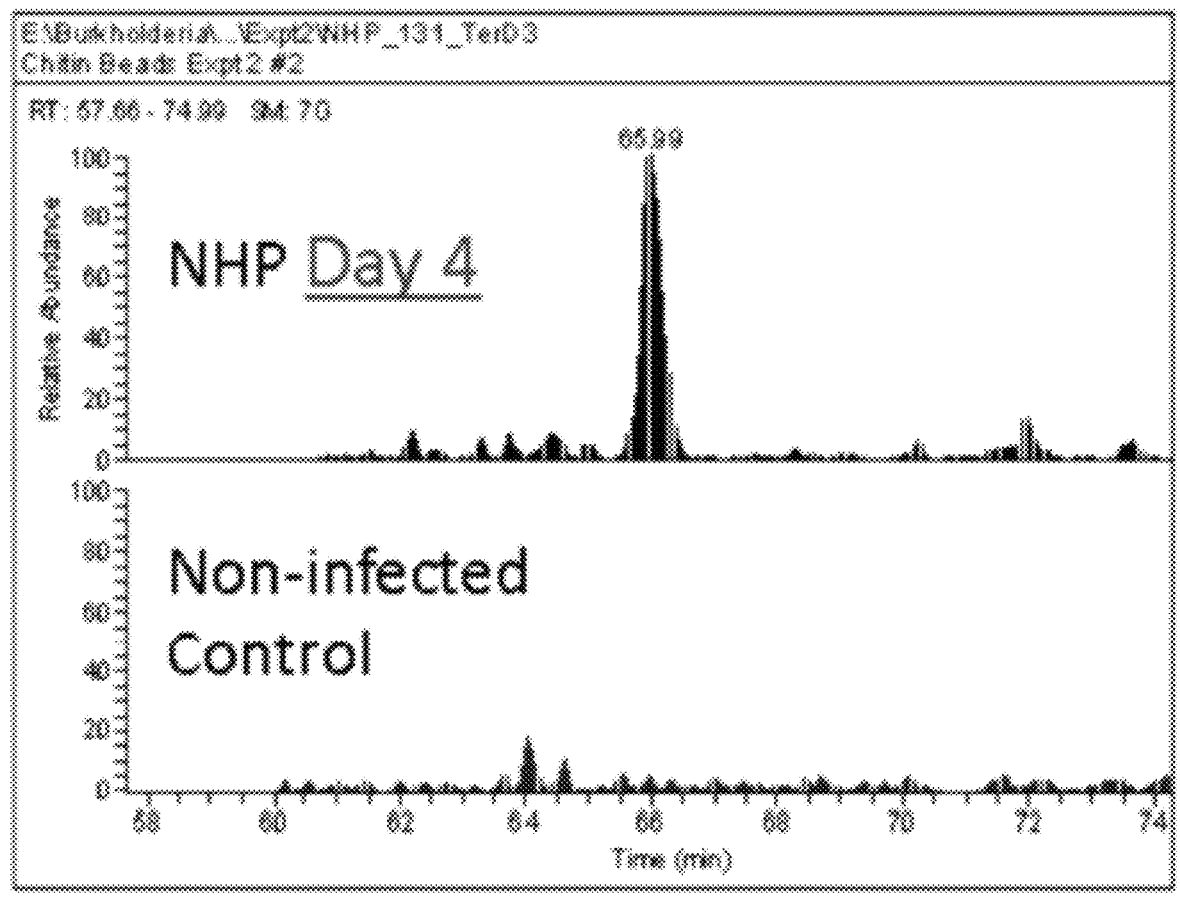
Figure 7:
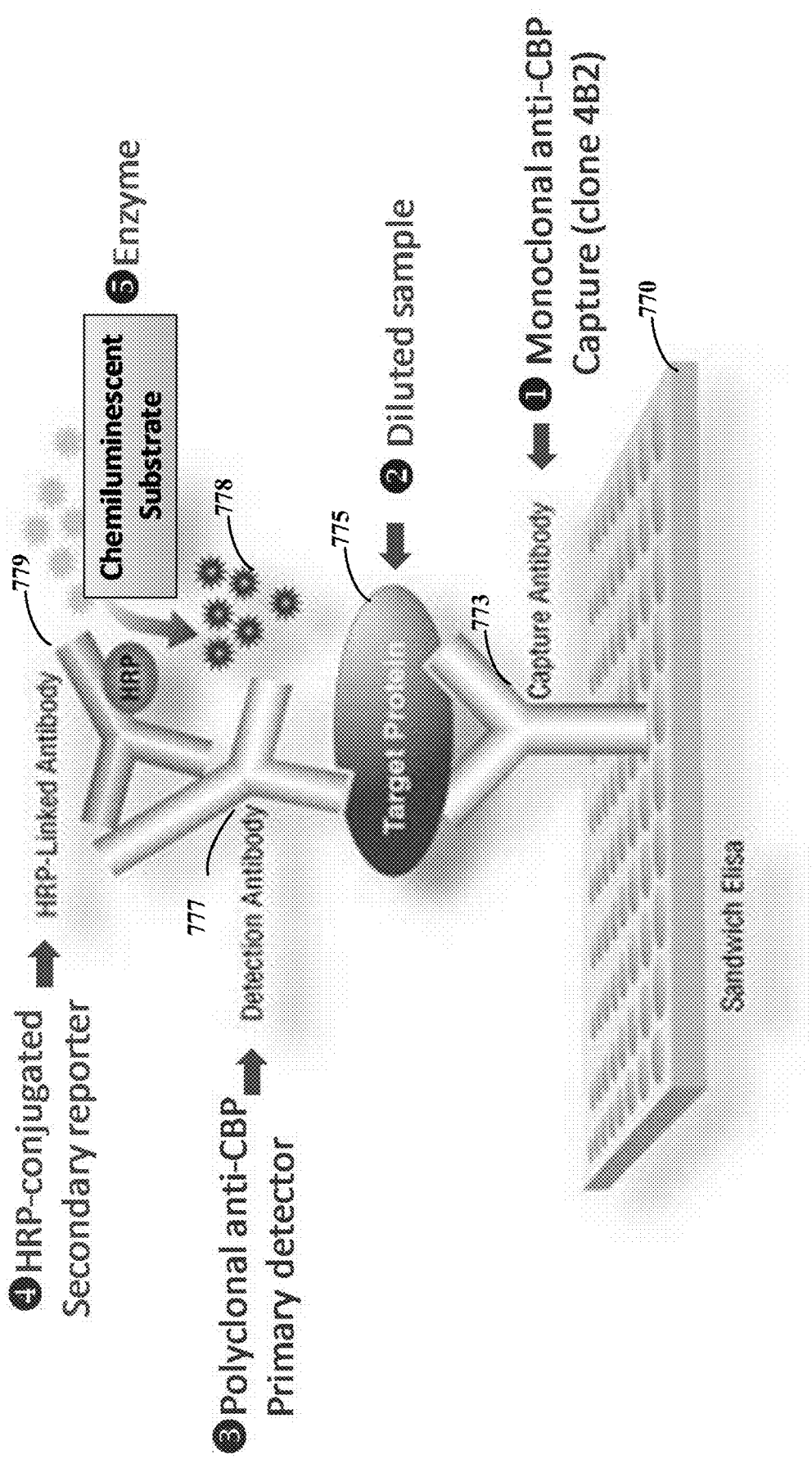
Figure 8A:
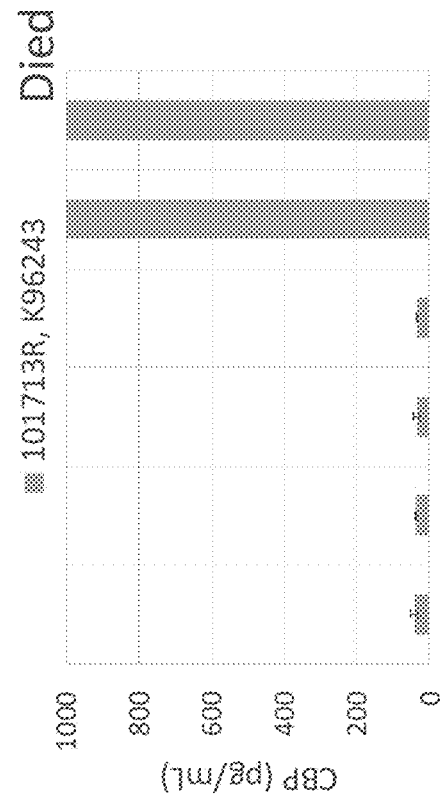
Figure 8B:
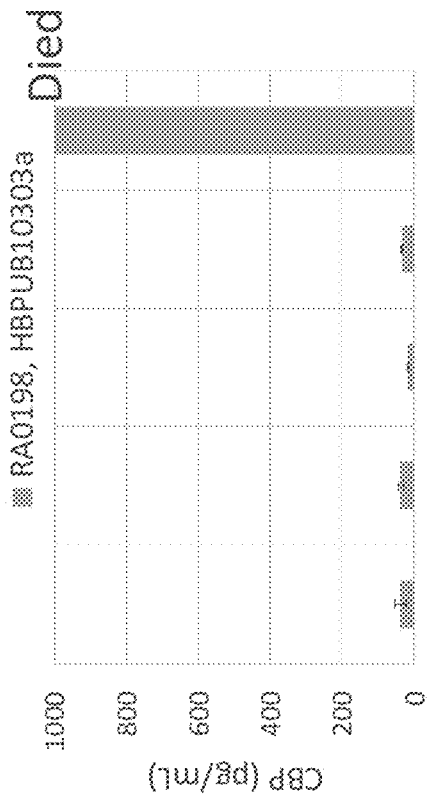
Figure 8C:
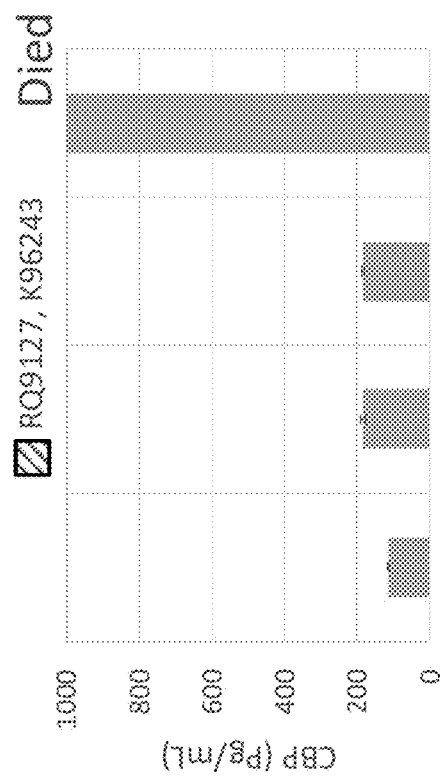
Figure 8D:
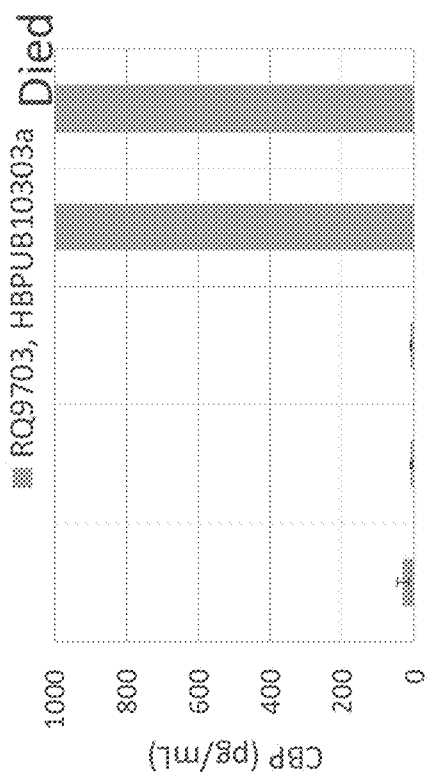
Figure 9:
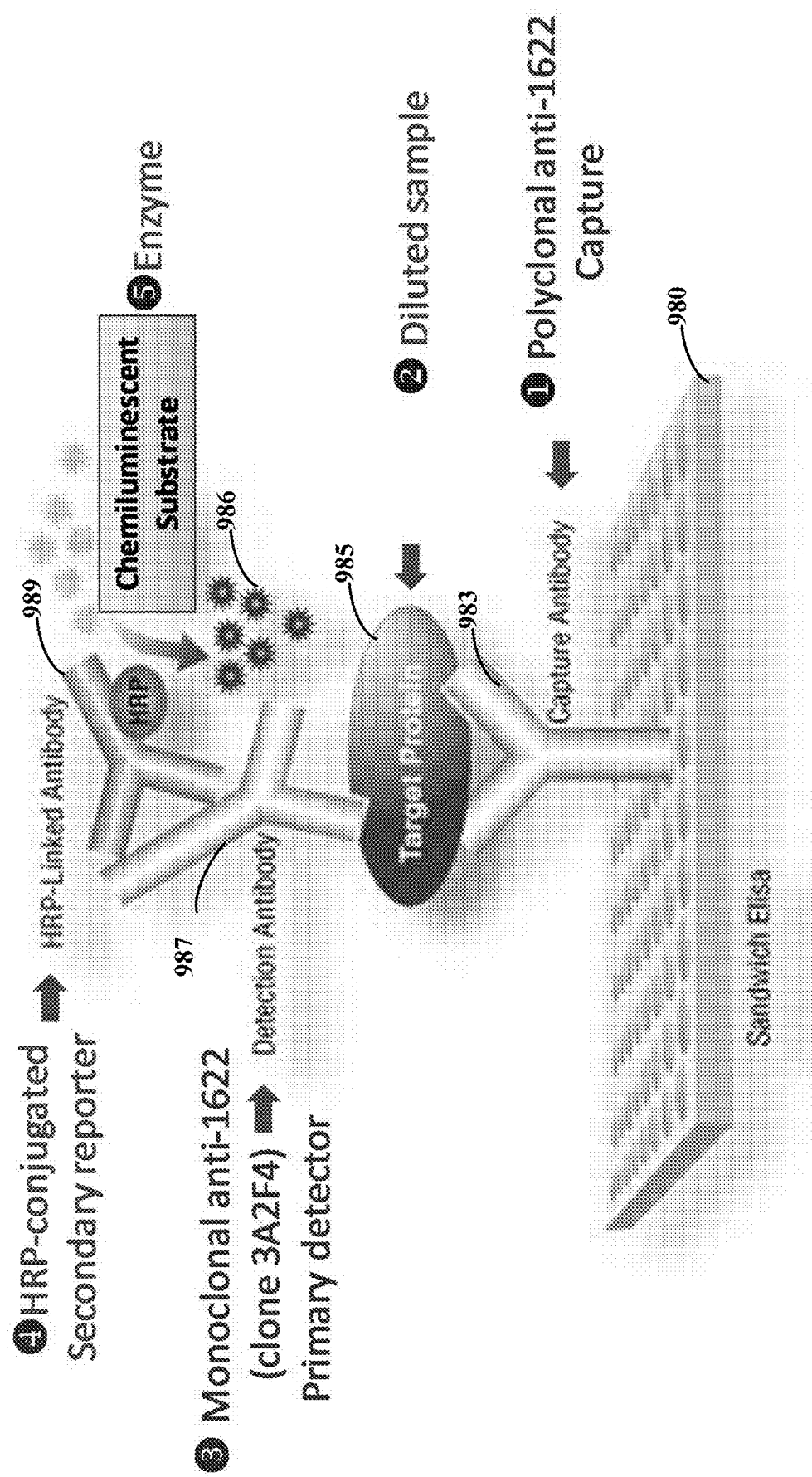
Figure 11:
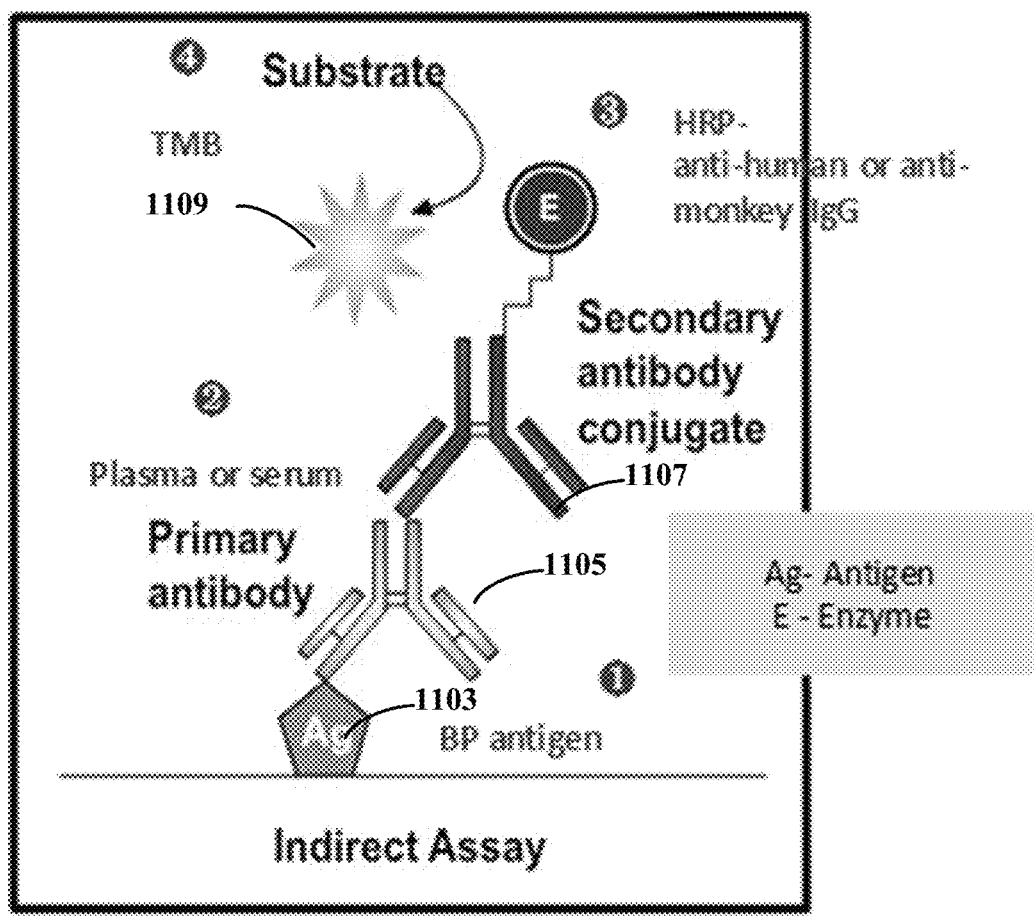
Figures 12A, 12B:
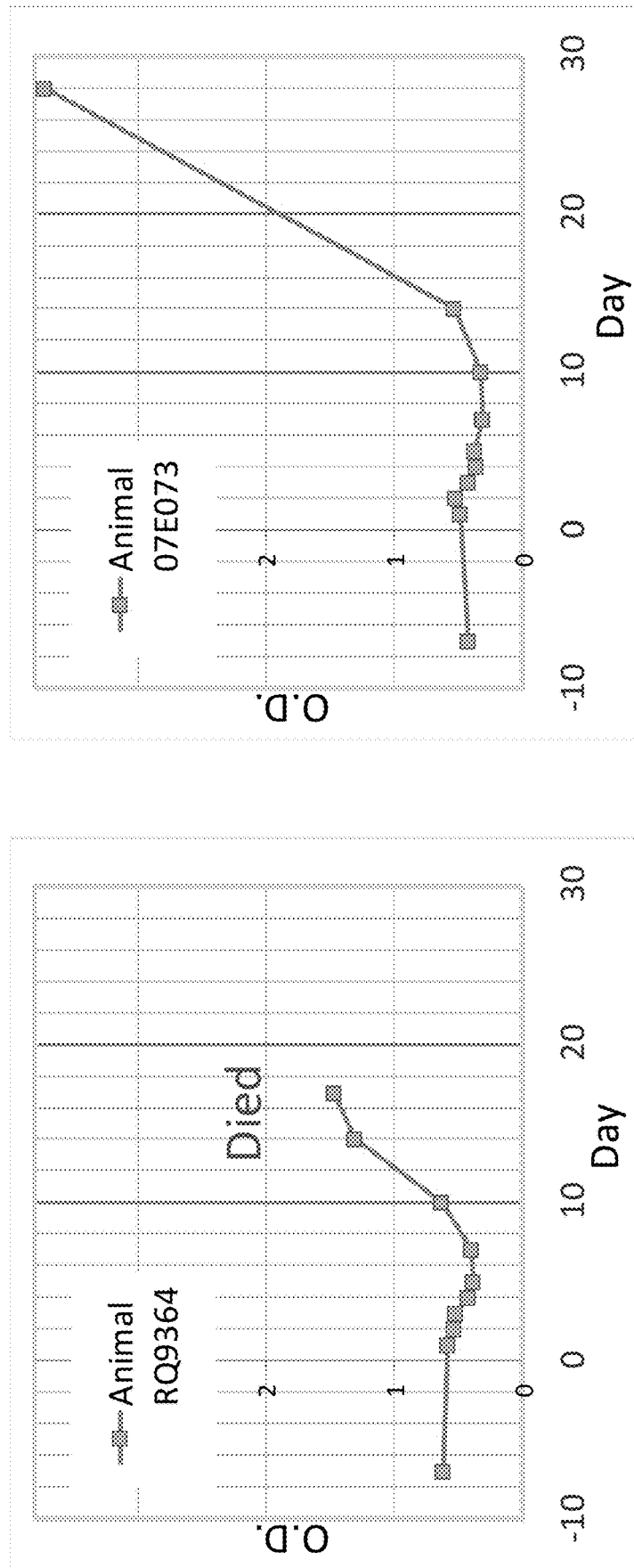
FIGS. 12A-12B illustrate an example of time profiles of IgG antibody response to the BP antigen, exported chitinase in (two) BP-infected NHPs, in accordance with various embodiments.
Figures 13A, 13B:
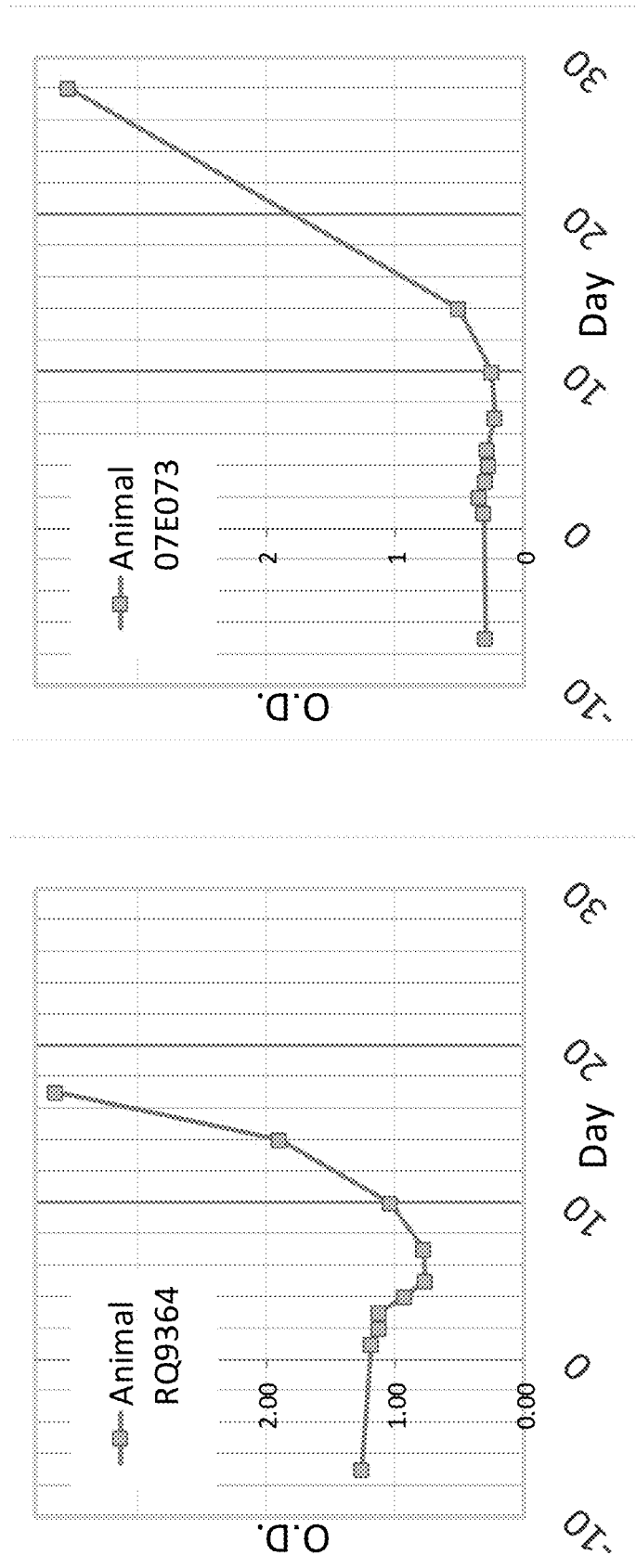
FIGS. 13A-13B illustrate an example time profile of IgG antibody response to the BP antigen, exported chitinase in the BP-infected NHPs, in accordance with various embodiments.
Figure 14B:
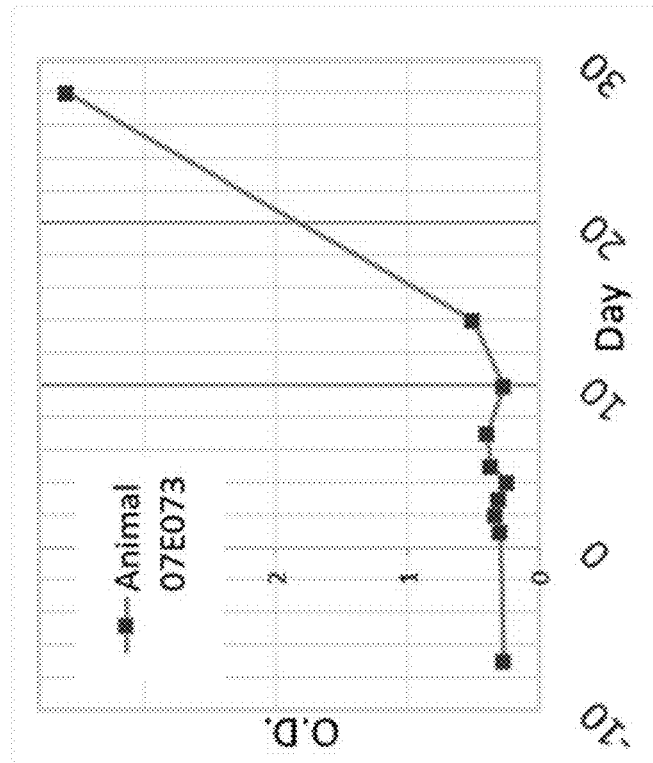
FIGS. 14A-14B illustrate an example time profile of IgG antibody response to the BP antigen, antigen, the BP hypothetical protein BPSL2703, in accordance with various embodiments.
Figure 14A:
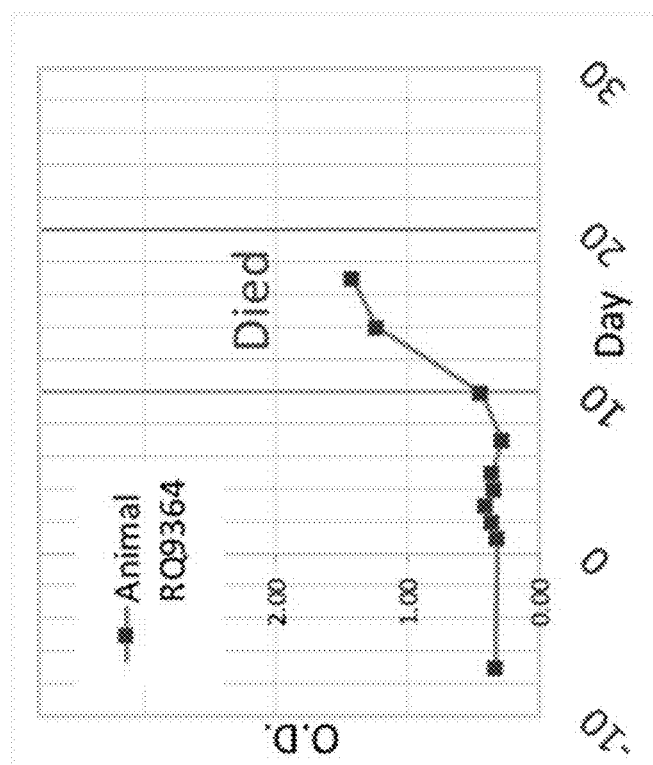
Figure 15:
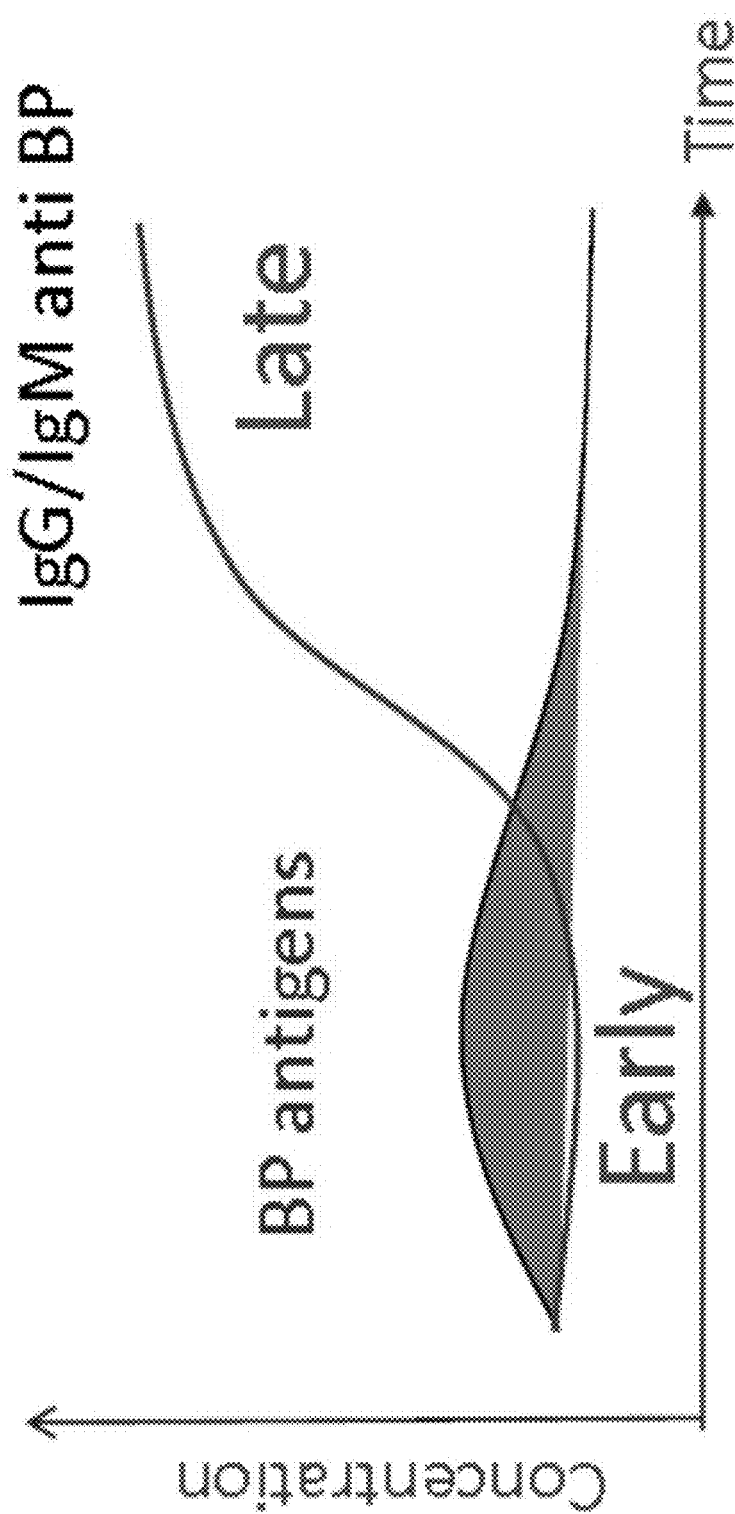

FIG. 15 illustrates a schematic example showing diagnostic sensitivity, in various embodiments, can be maximized by combining a plurality of the BP biomarkers with the host immune-response detection (e.g., IgG/IgM response).

As illustrated, various embodiments in accordance with the presence disclosure are related to the detection for the presence of BP using BP biomarkers associated with proteins secreted by BP. The BP biomarkers are identified in serum samples collected from a NHP infection-model such as with assay and LOD testing on the chitin-binding protein and the BPLS1622. Further, many of the identified proteins show antibody responses which demonstrates potential advantage by combining a plurality of the BP biomarkers with the host immune-response detection (e.g., IgG/IgM response) to maximize diagnostic sensitivity for patients.

Biomarker Confirmation by ELISA in a Pilot Set of Patient Sample Set

Table 5 summarizes results of detecting two candidate markers, BP CBP and BPSL1622 by ELISA in acute melioidosis patient samples for the first time. Using a cutoff threshold of 0.5 ng/mL for CBP or 0.7 ng/mL for BPSL1622, better detection sensitivity can be achieved with those two markers either alone (2 out of 5 acute melioidosis patients for CBP, 3 out of 5 for BPSL1622, or in combination (4 out of 5) than that of capsular polysaccharide (CPS) analyzed with the commercially available strips from InBIOS (0 out of 5), while none of the four non-melioidosis patients showed signal above the cutoff threshold. Although the sample set is limited, it indicates that the two markers shown herein might be the better pathogen marker for diagnosing acute melioidosis patients than the current commercially available rapid test.

TABLE 5

A summary of the pilot human sample analysis that shows the promise to detect the two leading candidate markers, BP CBP and BPSL1622 by ELISA in acute melioidosis patients for the first time.

| Sample List | BP CBP (ng/mL) | BPSL1622 (ng/mL) | CPS_InBIOS (Commercial Strip) | Cohort |
|---|---|---|---|---|
| MEL-S01-0082 | ND | 0.973 | ND | Group 1: Acute |
| MEL-S01-0514 | ND | 0.983 | ND | melioidosis; BP+ |
| MEL-S01-0579 | ND | ND | ND | positive in blood |
| MEL-S01-0764 | 0.060 | 0.640 | ND | culture |
| MEL-S01-0789 | 0.063 | 1.038 | ND | |
| MEL-S01-0052 | 0.043 | 0.578 | ND | Group 3: |
| MEL-S01-0072 | ND | 0.545 | ND | Non-melioidosis; BP- |
| MEL-S01-0078 | ND | 0.648 | ND | negative, but other |
| MEL-S01-0121 | ND | ND | ND | bacterial + |
| Acute melioidosis | 2 out of 5 | 3 out of 5 | 0 out of 5 | positive in |
| Non-melioidosis | 0 out of 4 | 0 out of 4 | 0 out of 5 | blood culture. |
| | ND (CBP) = 0.04 ng/mL | ND (1622) = 0.500 ng/mL | | |
| Cutoff for positive | >0.05 | >0.70 | Eye pos. | |
| Cutoff for negative | ≤0.05 | ≤0.70 | Eye neg. | |

As used herein, a BP biomarker includes or refers to class of polypeptides or other biomolecules released by pathogens. The set of BP biomarkers may be derived from molecules used by the organism to establish and maintain an infection, including those involved in evading host defenses, acquiring nutrients, and disseminating from an initial infection site during a case of melioidosis. In various embodiments, the BP biomarkers are polypeptides or proteins released from BP cells or that otherwise combine another molecule released from BP cells, such that testing for the presence of the biomarkers can be used to infer exposure to BP, infection caused by BP, and possible melioidosis diagnosis. A protein includes or refers to a biomolecule consisting of one or more chains of amino acids protein. A complete protein is usually folded into a three-dimensional structure. The three-dimensional structure can be formed by the primary structure (e.g., the amino acid sequence), the secondary structure (e.g., repeating local structures stabilized by hydrogen bonds, such as a-helixes, B-sheets, and turns), the tertiary structure (e.g., shape of a single protein molecule which includes the spatial relationship of secondary structures to one another and which are stabilized by nonlocal interactions) and the quaternary structure (e.g., formed from several protein molecules that function as a single protein complex). A polypeptide includes or refers to an organic polymer that includes a number of amino acids residues bonded together forming part of (or the whole) a protein. A hypothetical protein includes or refers to a protein that is not fully defined and/or the complete function of protein is unknown. Exposure of the biological sample to the antibody, when the biomarker is present within the sample, results in specific binding of the antigen in the biomarker (e.g., protein) by the antibody.

An agent includes or refers to substances, polypeptides, proteins or other molecules that specific to or otherwise binds to the BP biomarkers or another agent. The capture agent, in various embodiments, directly binds the BP biomarkers to a solid surface, effectively capturing the BP biomarkers. An agent that is specific to a biomarker includes or refers to an agent that binds to the biomarker. For example, the agent can be modified to include a component or portions designed to specific bind to the biomarker. A detection agent includes or refers to polypeptides, proteins, or other molecules configured to bind to one of the BP biomarkers or to the capture agent and is detectable. Example detection agents include a label bound to the capture agent itself, a second antibody having a label, an anti-antibody having a label, and other types of molecular tags, such as a molecule with a unique sequence or weight. Example labels include fluorescent, enzymatic and/or radioactive labels, although embodiments are not so limited. In some embodiments, the capture agent includes the detection agent (and can be used interchangeably) and in other embodiments they are separate. For example, the capture agent can be an antibody bound to a label and can specifically bind to one of the BP biomarkers. The binding of the capture agent can be directly detected via the label, and thereby the capture agent can be considered a detection agent as well. As used herein, "immobilized to" includes or refers to an attachment, in a fixed manner, of an agent, biomarker or other molecule to a solid support, such as a surface or substrate. "Conjugated to" includes or refers to a reversible attachment or combining of an agent, biomarker or other molecule. "Adherent to" includes or refers to a temporarily attachment of an agent, biomarker or other molecule to a solid support in such a way that the agent, biomarker or other molecule is released into the sample solution during or after application of the sample.

An antibody includes or refers to proteins used by the immune system to detect, neutralize, and/or kill various target cells, such as tumor cells and pathogens, which may be harmful to the host organism. One or more of the antibodies can be a monoclonal antibody. Antibodies bind by means of specific binding sites to specific antigenic determinants or epitopes on antigens (e.g., to the BP biomarkers). An epitope, as used herein, includes or refers to an antigenic determinant. An epitope can be part of the antigen (e.g., protein or other biomolecule released or secreted by BP cells) that is recognized by the immune system and further specially binds to antibodies, B-cells and/or T-cells. A secondary antibody includes or refers to an antibody that binds to another epitope of the antigen, to the (capture or primary) antibody, or in some specific embodiments, to the same epitope as the (capture or primary) antibody such as with BP biomarkers that may have multiple of the same epitope. An anti-antibody includes or refers to an antibody that binds to another antibody.

Various embodiments are implemented in accordance with the underlying Provisional Application (Ser. No. 62/849,607), entitled "Biomarkers for Detection of *Burkholderia Pseudomallei*," filed May 17, 2019 to which benefit is claimed and which is fully incorporated herein by reference for it general and specific teachings, and including the respective Tables references above. For instance, embodiments herein and/or in the provisional application can be combined in varying degrees (including wholly). Reference can also be made to the experimental teachings and underlying references provided in the underlying Provisional Applications. Embodiments discussed in the Provisional Applications are not intended, in any way, to be limiting to the overall technical disclosure, or to any part of the claimed disclosure unless specifically noted.

Based upon the above discussion and illustrations, those skilled in the art will readily recognize that various modifications and changes may be made to the various embodiments without strictly following the exemplary embodiments and applications illustrated and described herein without departing from the true spirit and scope of various aspects of the disclosure, including aspects set forth in the claims.

What is claimed is:

1. A method comprising:
    causing a physical interaction between a biological sample from a subject and a set of first agents by exposing the biological sample to the set of first agents, the set of first agents being specific to a set of *Burkholderia pseudomallei* (BP) biomarkers associated with proteins released from BP or associated with other molecules released from BP, wherein the set of BP biomarkers is associated with at least a chitin-binding protein BPSS0493 and a protein BPSL1622; and
    determining a presence of BP in the biological sample based on detected binding between the one or more of the set of first agents and the one or more of the set of BP biomarkers within twenty-four hours of causing the physical interaction.

2. The method of claim 1, wherein the set of BP biomarkers is associated with proteins including at least the chitin-binding protein BPSS0493, the protein BPSL1622, a protein BPSL2703, and an exported chitinase protein BPSL1763, and the set of first agents are used to form an assay for the set of BP biomarkers having and analytical sensitivity to the set of BP biomarkers of at least one nanogram/milliliter.

3. The method of claim 1, further including, in response to determining the presence of BP in the biological sample, administering an antimicrobial agent to the subject for treating a melioidosis infection.

4. The method of claim 1, wherein:
    causing the physical interaction includes binding an antibody to at least one of the set of BP biomarkers, wherein the set of first agents include the antibody bound to a label; and
    determining the presence of BP in the biological sample includes determining the physical interaction occurred by identifying the presence of the label after processing.

5. The method of claim 1, wherein:
    causing the physical interaction includes binding at least some of the set of first agents to one or more of the set of BP biomarkers and binding one or more of a set of second agents to the one or more of the set of first agents or an epitope of one or more of the proteins, and
    determining the presence of BP in the biological sample includes identifying the presence of at least a portion of the set of second agents.

6. The method of claim 5, wherein the set of first agents include a first antibody and the one or more of the set of second agents include a second antibody bound to a label, and the method further includes exposing the biological sample to the second antibody and, therein, binding the second antibody to the protein.

7. The method of claim 5, wherein the set of first agents include a first antibody and the one or more of the set of second agents include a second antibody bound to a label, and the method further includes exposing the biological sample to the second antibody and, therein, binding the second antibody to the first antibody.

8. The method of claim 1, wherein:
    causing the physical interaction includes exposing the biological sample to a plurality of solid supports, each of the plurality of solid supports bound to at least one of the set of first agents; and
    determining the presence of BP in the biological sample includes identifying agglutination of the plurality of solid supports.

9. The method of claim 1, wherein the set of first agents includes a first antibody specific to a first BP biomarker of the set of BP biomarkers, and wherein causing the physical interaction includes:
    applying the first antibody to the biological sample, wherein the presence of the BP biomarker within biological sample causes binding of the first antibody to the first BP biomarker; and
    applying a label-containing second antibody to the biological sample, the label-containing second antibody being specific to an epitope of the first antibody or an epitope of one of the proteins associated with the first BP biomarker, wherein the first and the label-containing second antibodies are man-made monoclonal antibodies.

10. The method of claim 1, wherein the determining of the presence of BP within the biological sample includes detecting a melioidosis infection in the subject in less than twenty-four hours from causing the physical interaction.

11. The method of claim 1, wherein the set of first agents includes a first antibody and causing the physical interaction between the biological sample and the set of first agents includes exposing the biological sample to a plurality of antibodies, the plurality of antibodies including the first antibody specific to a first BP biomarker of the set of the BP biomarkers associated with a first protein of the proteins and a second antibody specific to a second BP biomarker of the set of BP biomarkers associated a second protein of the proteins.

12. The method of claim 1, wherein determining the presence of BP in the biological sample further includes exposing the set of BP biomarkers to the biological sample and identifying the presence of immunoglobulin molecules reactive with the set of BP biomarkers in the biological sample, wherein each BP biomarker of the set of BP biomarkers has a diagnostic sensitivity of at least sixty percent.

13. A kit for detecting a presence of *Burkholderia pseudomallei* (BP), the kit comprising:
    a solid support;
    a set of first agents to bind to a set of BP biomarkers associated with proteins released from BP or associated with other molecules released from BP as present in a biological sample obtained from a subject, wherein the set of BP biomarkers is associated with at least a chitin-binding protein BPSS0493 and a protein BPSL1622; and
    a set of labels to bind to the proteins, the solid support to receive application of the biological sample, the set of first agents, and the set of labels, and in response to the application, a presence of the BP biomarker causes accumulation of one or more of the set of labels bound to the solid support and indicates the presence of BP in the biological sample within twenty-four hours of the application of the biological sample.

14. The kit of claim 13, further including a set of second agents to bind the set of labels to the proteins, wherein the solid support is to further receive application of the set of second agents.

15. The kit of claim 13, further including a set of second agents bound to the set of labels, the set of second agents to bind to one or more of the set of first agents, thereby binding the one or more of the set of labels to the proteins, wherein the solid support is to further receive application of the set of second agents.

16. The kit of claim 13, wherein each of the set of BP biomarkers has a diagnostic sensitivity of at least sixty percent, and wherein subsets of the set of first agents are specific to different ones of the set of BP biomarkers associated with the proteins released from BP.

17. The kit of claim 13, wherein the set of BP biomarkers are associated proteins selected from the group consisting of: the chitin-binding protein BPSS0493, the protein BPSL1622, a protein BPSL2703, and an exported chitinase protein BPSL1763.

18. An apparatus comprising:
reagents including a set of first agents and a set of second agents; and
a solid support including:
a first region to receive a biological sample obtained from a subject;
a second region including the set of first agents, each bound to a label, the set of first agents being adherent on the second region and being specific to a set of *Burkholderia pseudomallei* (BP) biomarkers associated with proteins released from BP or associated with other molecules released from BP, wherein the set of BP biomarkers is associated with at least a chitin-binding protein BPSS0493 and a protein BPSL1622; and
a third region including the set of second agents immobilized to the third region and being specific to the proteins,
wherein in response to receipt of the biological sample,
the first region is to pass a portion of the biological sample to the second region, the second region is to pass at least some of the portion of the biological sample to the third region; and
the presence of the BP biomarker causes accumulation of the label in the third region indicating a presence of BP in the biological sample within twenty-four hours from application of the biological sample.

19. The apparatus of claim 18, wherein the second region includes a conjugate that includes the set of first agents and a salt-sugar matrix that binds the set of first agents to the second region, wherein the salt-sugar matrix is to dissolve in response to the portion of the biological sample passing to the second region, thereby releasing the portion of the set of first agents and allowing for migration to the third region.

20. The apparatus of claim 18, further including one or more additional regions containing immobilized control agents that bind to the set of first agents, and wherein the set of BP biomarkers is associated with proteins comprising the chitin-binding protein BPSS0493, the protein BPSL1622, a protein BPSL2703, and an exported chitinase protein BPSL1763.

\* \* \* \* \*